United States Patent
Jain et al.

(10) Patent No.: US 8,217,154 B2
(45) Date of Patent: Jul. 10, 2012

(54) ACTIVATED SIALIC ACID DERIVATIVES FOR PROTEIN DERIVATISATION AND CONJUGATION

(75) Inventors: Sanjay Jain, London (GB); Ioannis Papaioannou, London (GB); Smita Thobhani, London (GB)

(73) Assignee: Lipoxen Technologies Limited, London (GB)

( * ) Notice: Subject to any disclaimer, the term of this patent is extended or adjusted under 35 U.S.C. 154(b) by 793 days.

(21) Appl. No.: 11/816,823

(22) PCT Filed: Feb. 16, 2006

(86) PCT No.: PCT/GB2006/000540
§ 371 (c)(1),
(2), (4) Date: Aug. 21, 2007

(87) PCT Pub. No.: WO2006/090119
PCT Pub. Date: Aug. 31, 2006

(65) Prior Publication Data
US 2008/0262209 A1    Oct. 23, 2008

(30) Foreign Application Priority Data

Feb. 23, 2005  (EP) ..................................... 05251017
Aug. 12, 2005  (GB) ....................... PCT/GB05/03160

(51) Int. Cl.
*C08B 37/00*    (2006.01)
*C07H 15/26*    (2006.01)
(52) U.S. Cl. ..................................... 536/17.4; 536/18.7
(58) Field of Classification Search .................. 536/17.4, 536/18.7
See application file for complete search history.

(56) References Cited

U.S. PATENT DOCUMENTS

| 4,225,487 A | 9/1980 | Cuatrecasas et al. |
| 5,534,259 A | 7/1996 | Zalipsky et al. |
| 6,680,054 B1 | 1/2004 | Reece et al. |

FOREIGN PATENT DOCUMENTS

| EP | 0 273 388 | 7/1988 |
| EP | 0 371 495 | 6/1990 |
| WO | WO 92/22331 A1 * | 12/1992 |
| WO | WO-2005/016973 | 2/2005 |
| WO | WO 2005/016973 A1 * | 2/2005 |
| WO | WO-2006/016168 | 2/2006 |

OTHER PUBLICATIONS

International Search Report for PCT/GB2006/000540, mailed on May 26, 2006, 3 pages.
Fan et al., Journal of Organic Chemistry (2002) 67:7565-7568.
Sofia, Molecular Diversity (1998) 3:75-94.
International Preliminary Report on Patentability for PCT/GB2006/000540, date mailed on Aug. 28, 2007, 7 pages.

* cited by examiner

*Primary Examiner* — Shaojia Anna Jiang
*Assistant Examiner* — Ganapathy Krishnan
(74) *Attorney, Agent, or Firm* — Annette S. Parent; Ralf Fang; Morgan, Lewis & Bockius, LLP

(57) ABSTRACT

Derivatives of PSAs are synthesized, in which a reducing and/or non-reducing end terminal sialic acid unit is transformed into a N-hydroxysuccinimide (NHS) group. The derivatives may be reacted with substrates, for instance substrates containing amine or hydrazine groups, to form non-cross-linked/crosslinked polysialylated compounds. The substrates may, for instance, be therapeutically useful drugs, peptides or proteins or drug delivery systems.

14 Claims, 21 Drawing Sheets

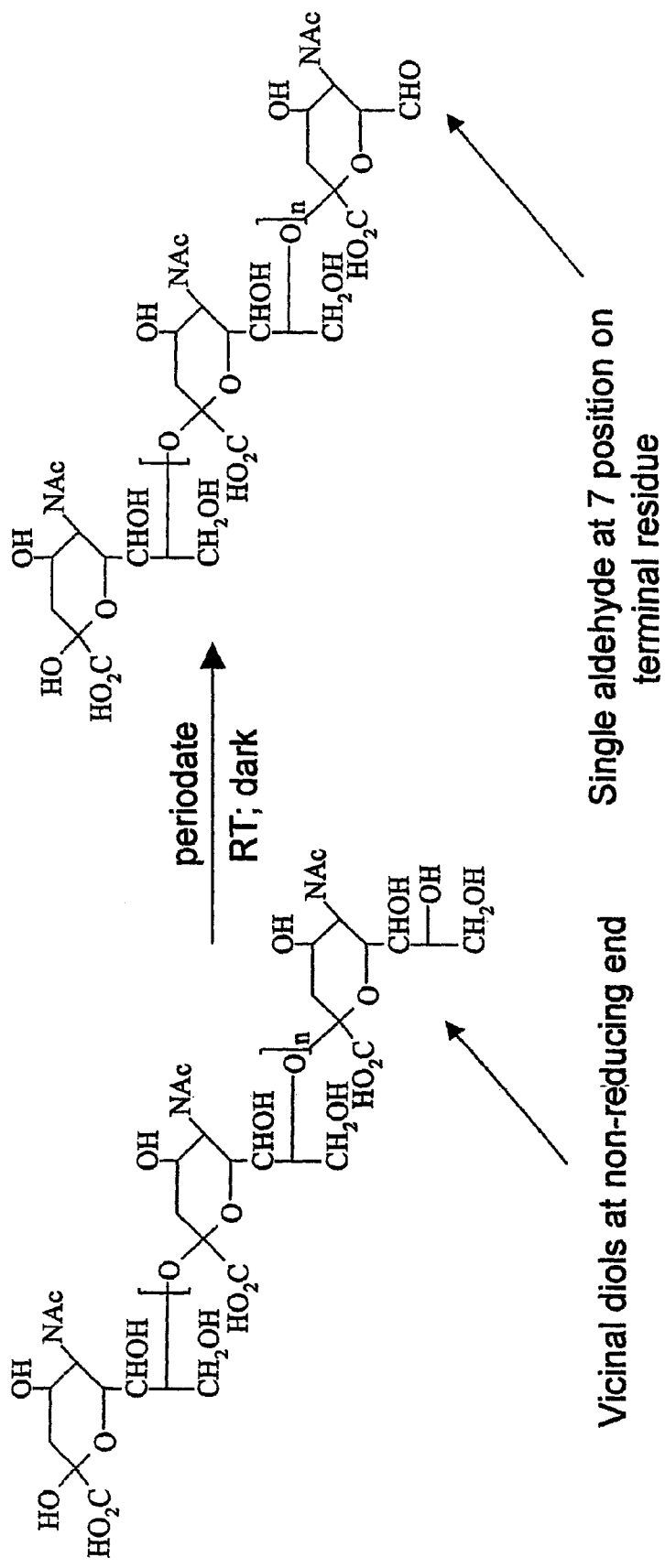
Figure 1a. Current state of the art of protein derivatisation with polysialic acid; a) oxidation of colominic acid (a form of polysialic acid) with sodium periodate to form a protein-reactive aldehyde at the non-reducing end.

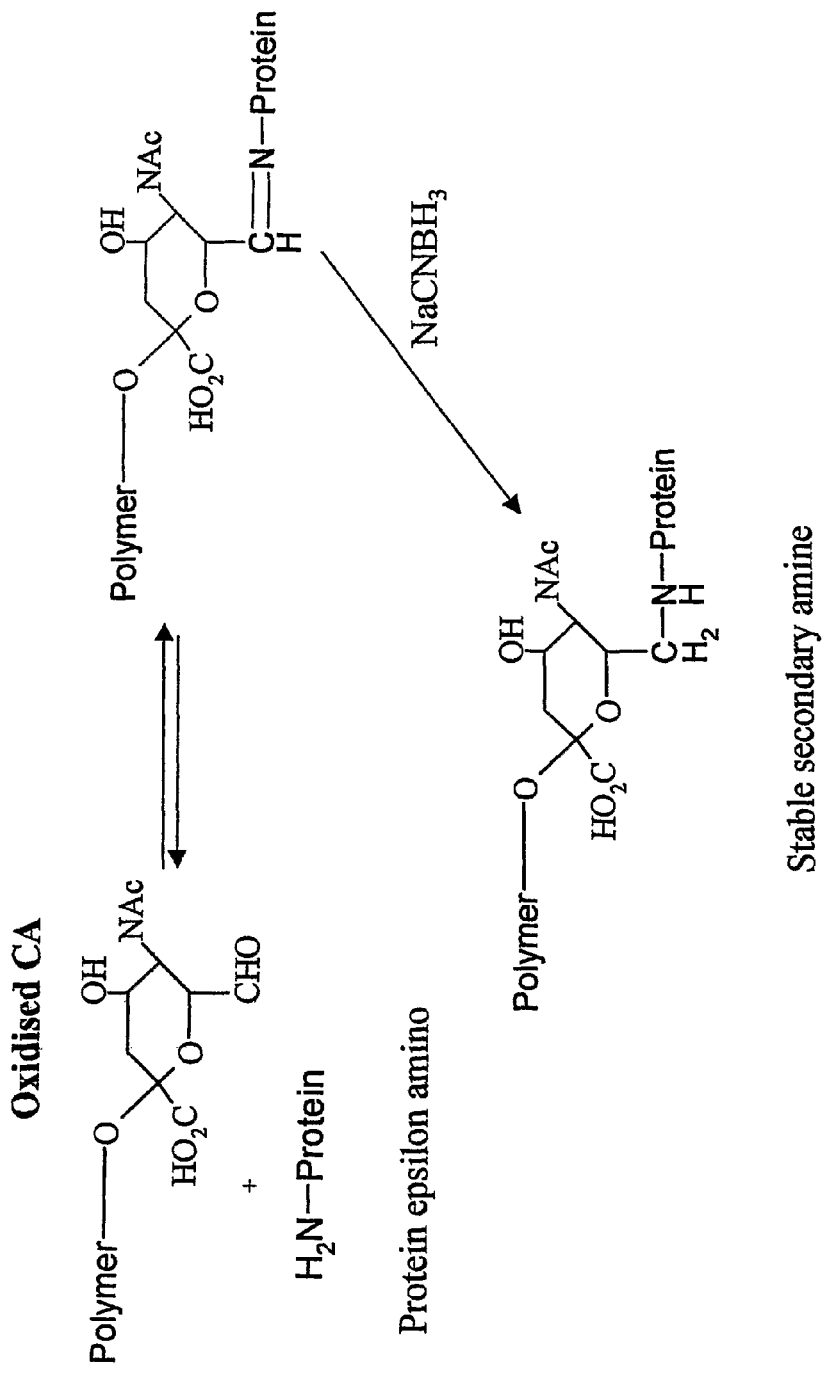
Figure 1b.Current state of the art of protein derivatisation with polysialic acid; b) selective reduction of the Schiff's base with cyanoborohydride to form a stable irreversible covalent bond with the protein amino group.

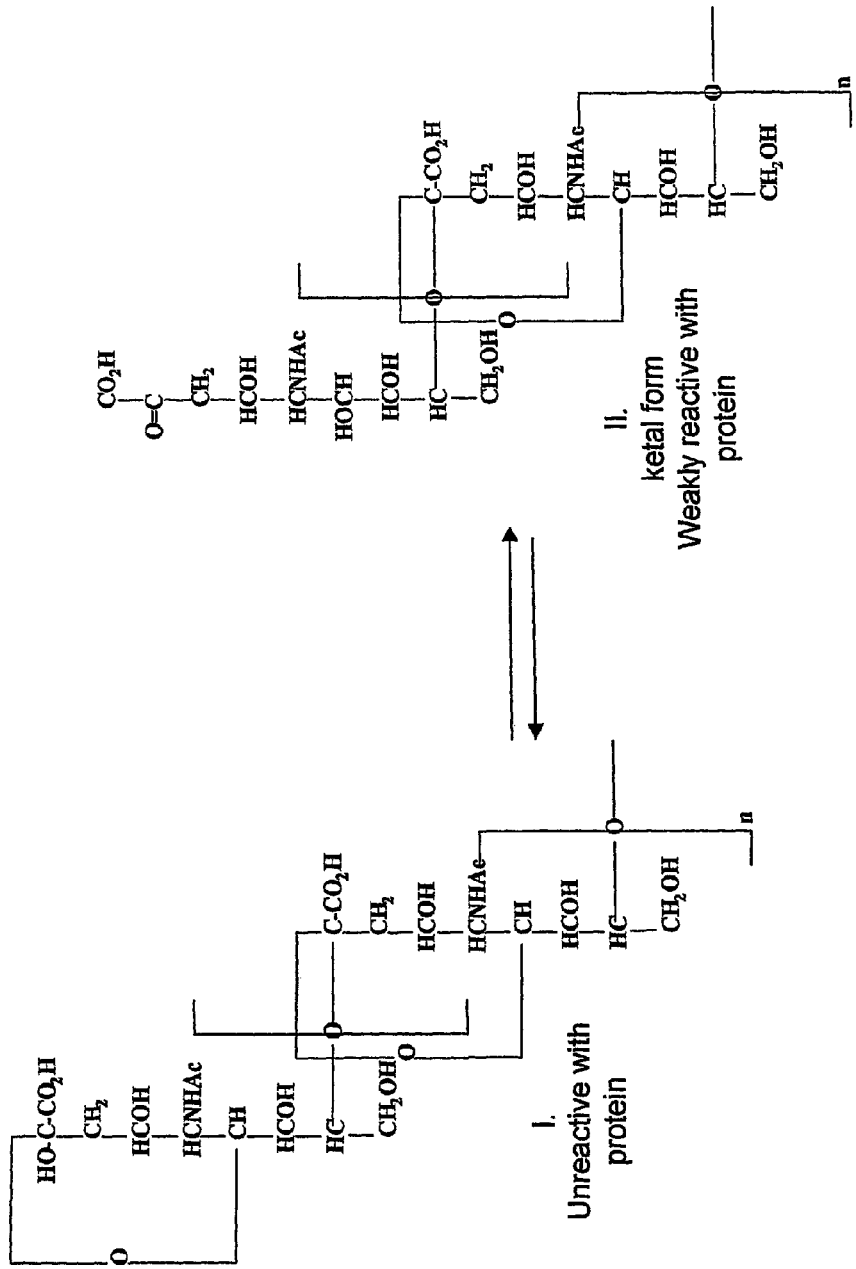

Fig 3. Tautomeric equilibrium of poly-alpha-2,8-linked N-acetylneuraminic acid (a PSA)
In solution, the terminal sialic acid residue at the reducing end of polysialic acid exists in a tautomeric equilibrium. The ketal form, although in low abundance in the equilibrium mixture (Jennings and Lugowski, 1981) is weakly reactive with protein amine groups, and can give rise to covalent adducts with proteins in the presence of sodium cyanoborohydride, although at a rate and to an extent that are not practically useful.

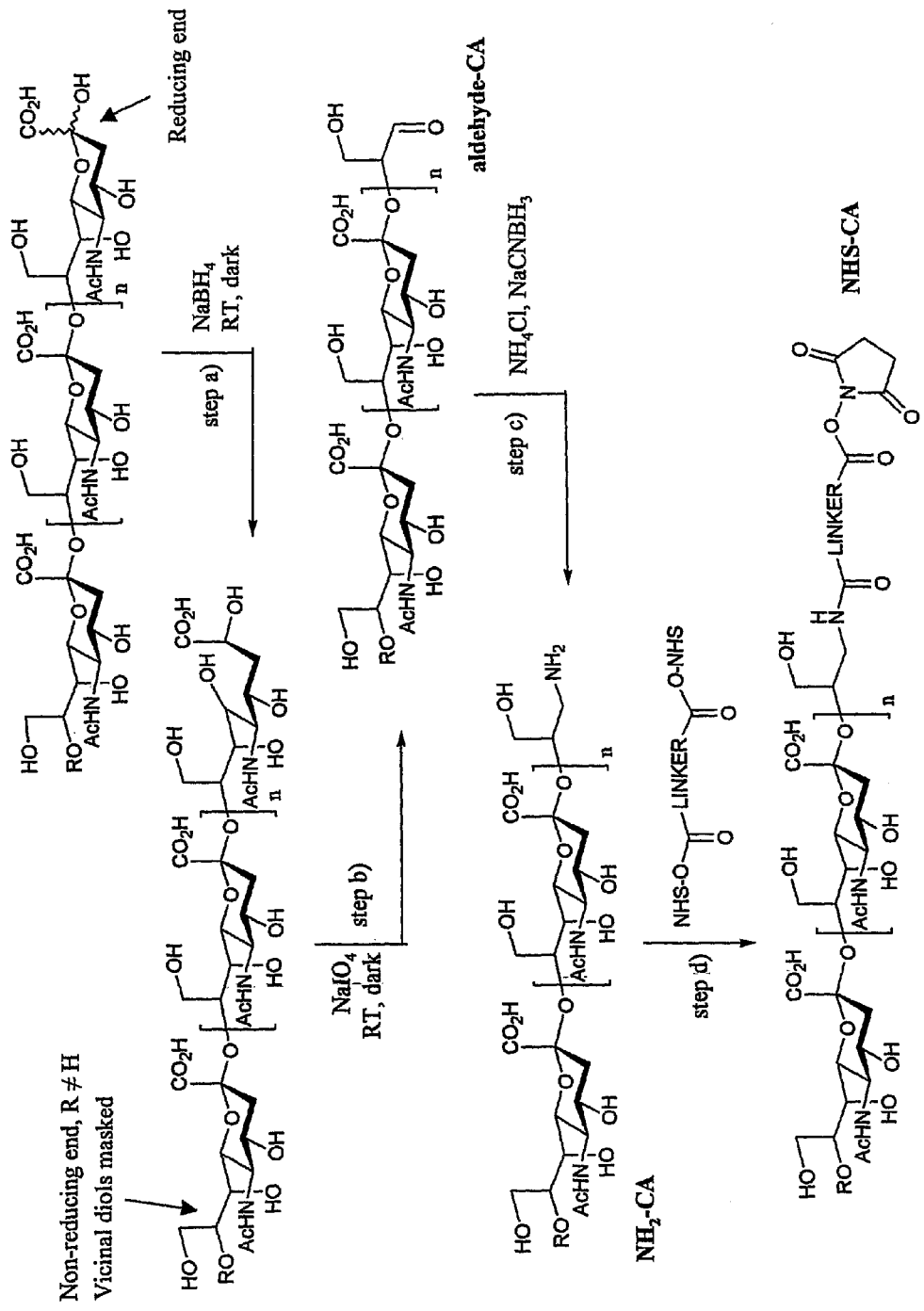
Figure 4: Preparation of reducing end derivatised NHS-CA

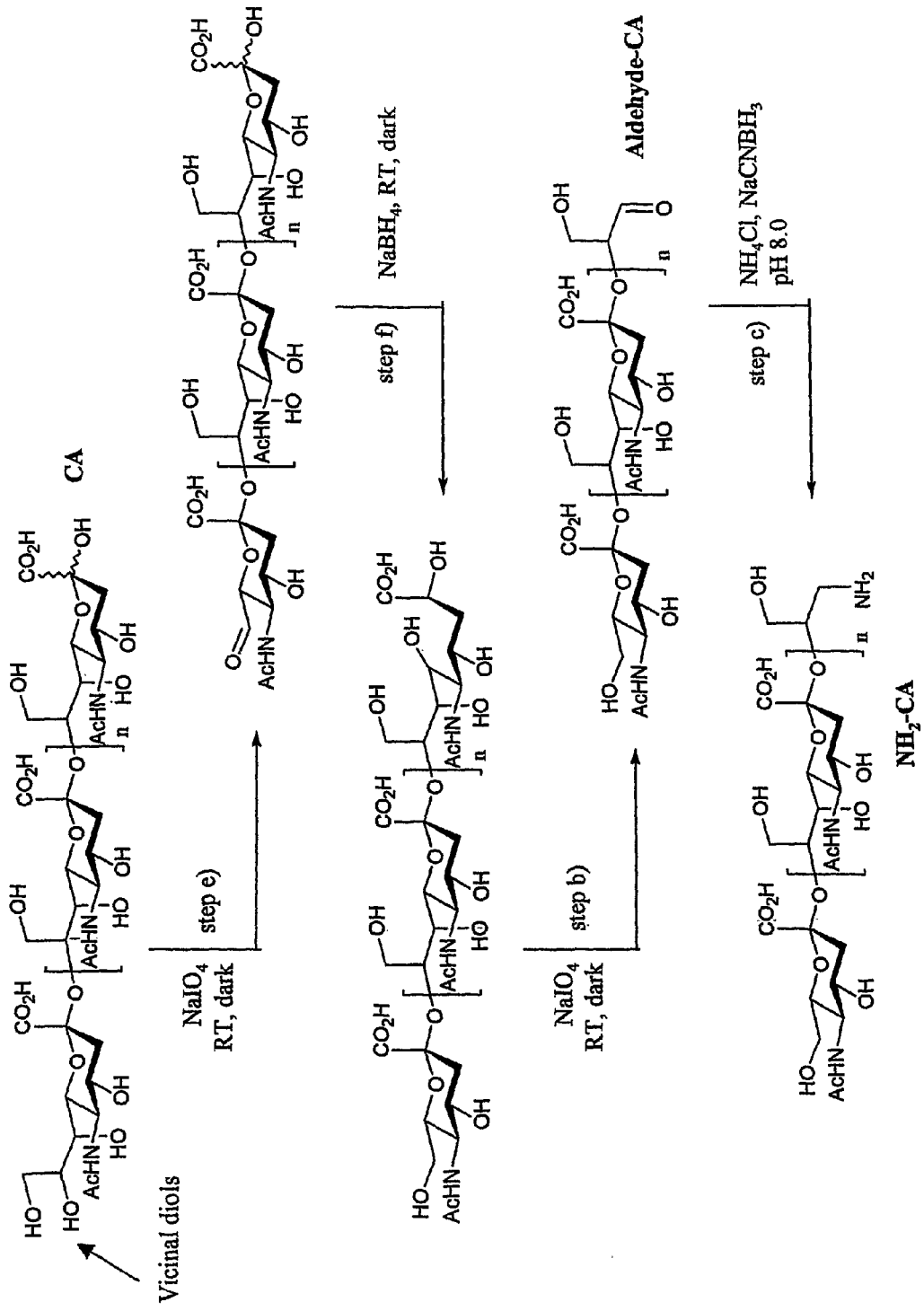
Figure 5: Preparation of reducing end derivatised CA

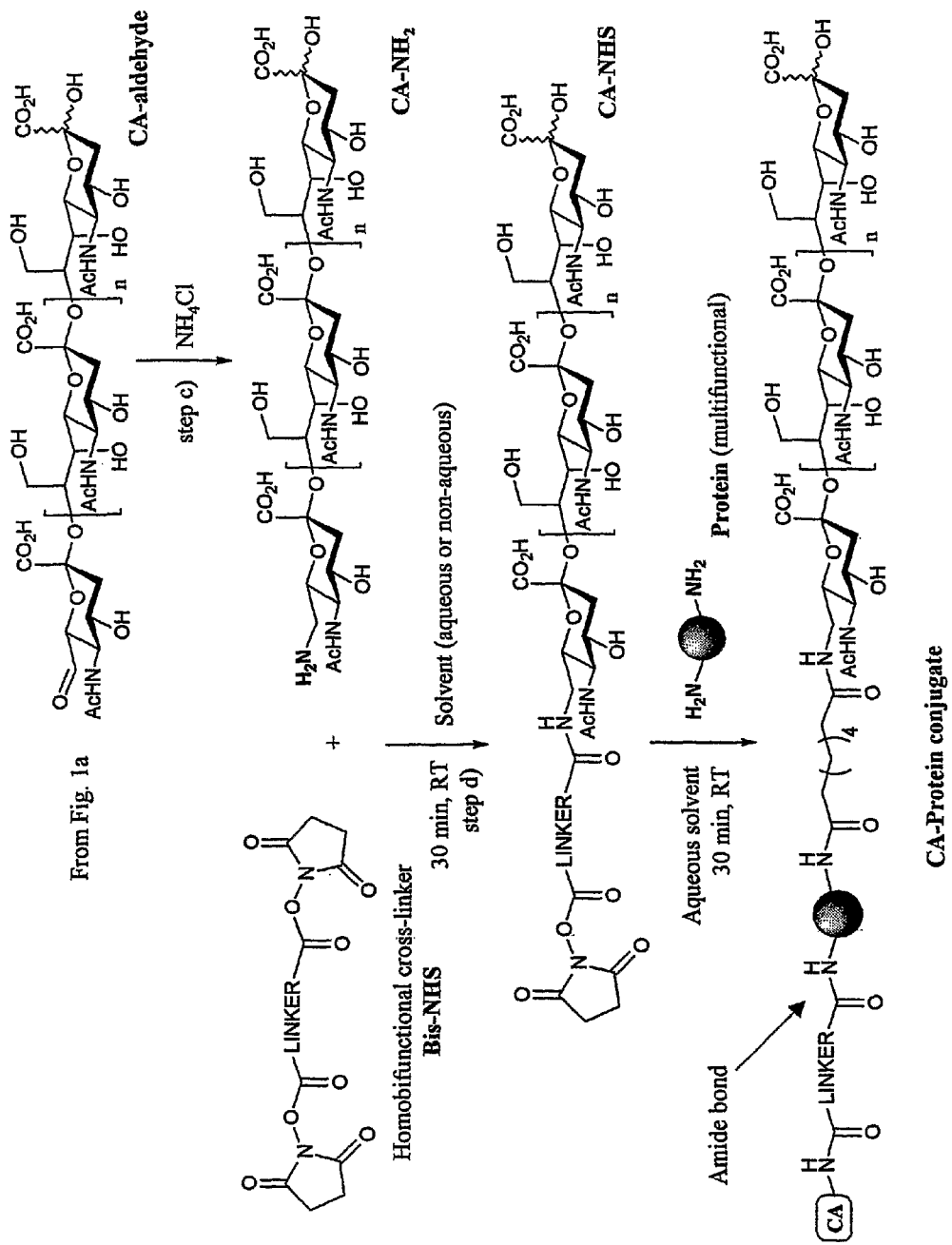
Figure 6: General Scheme for CA-protein conjugation using NHS esters

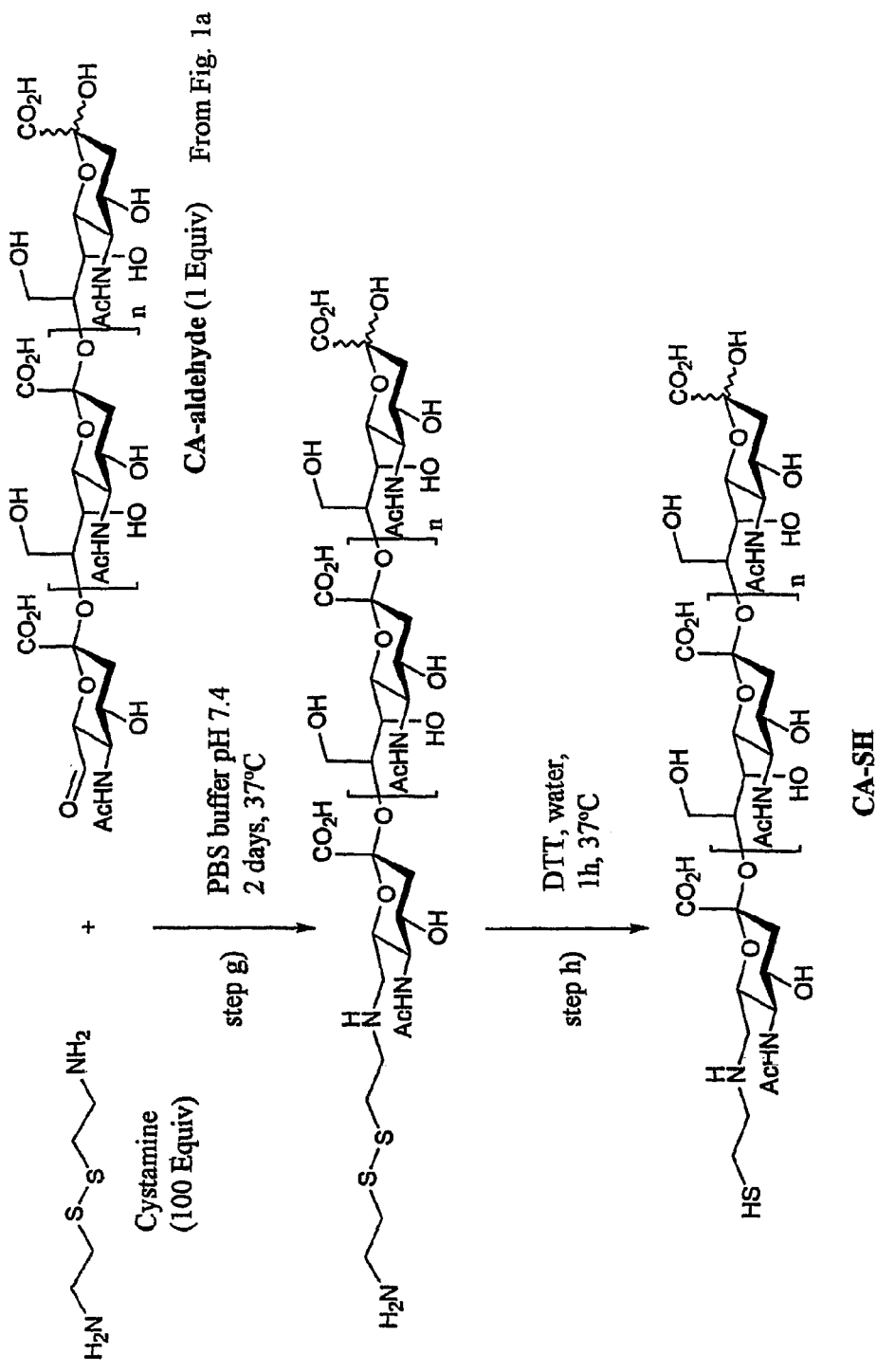
Figure 7a: Preparation of derivatised CA-SH at non-reducing end

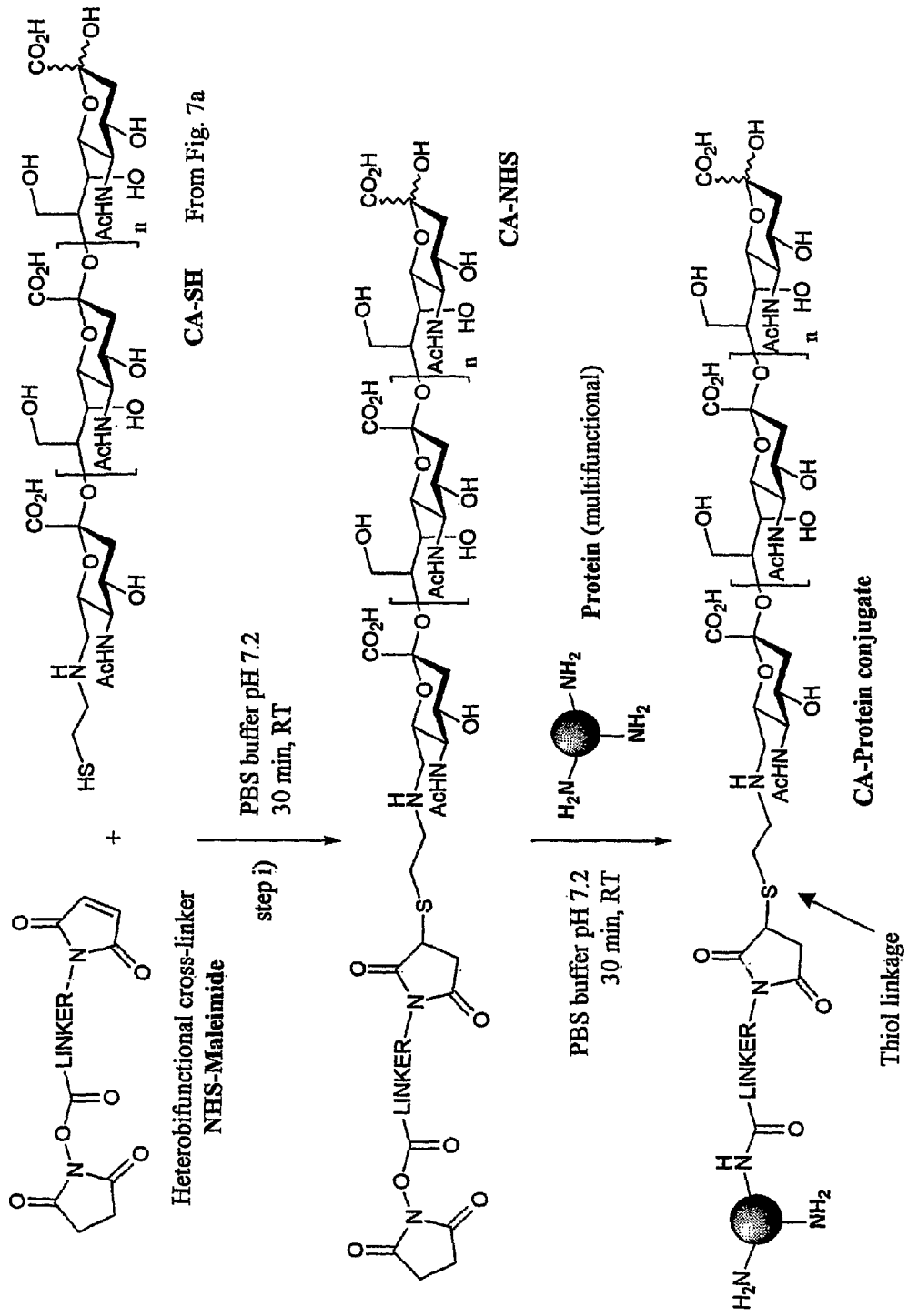
Figure 7b: Schematic representation of CA-protein conjugation using NHS-maleimide

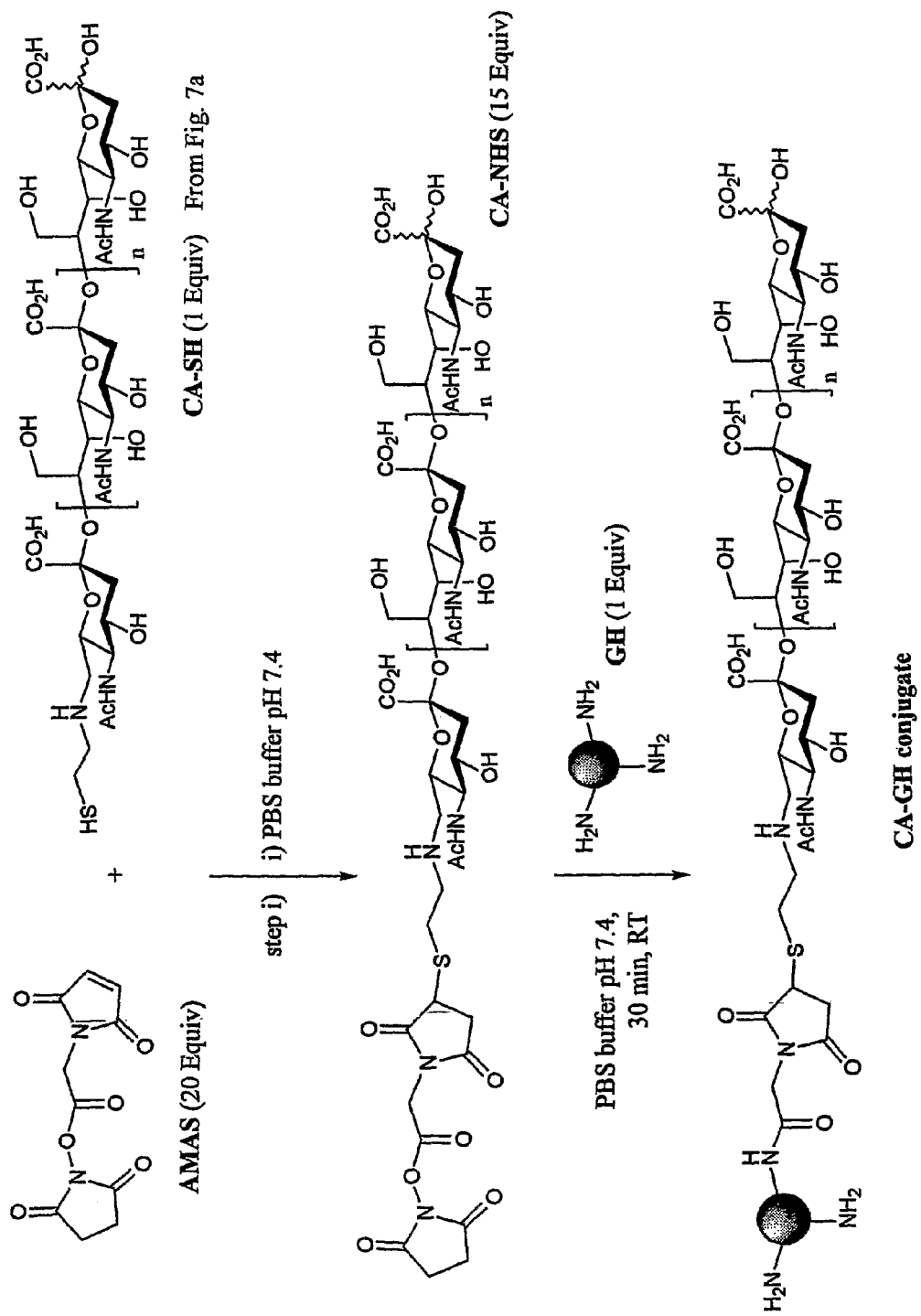
Figure 7c: Preparation of CA-protein conjugates using NHS-maleimide AMAS

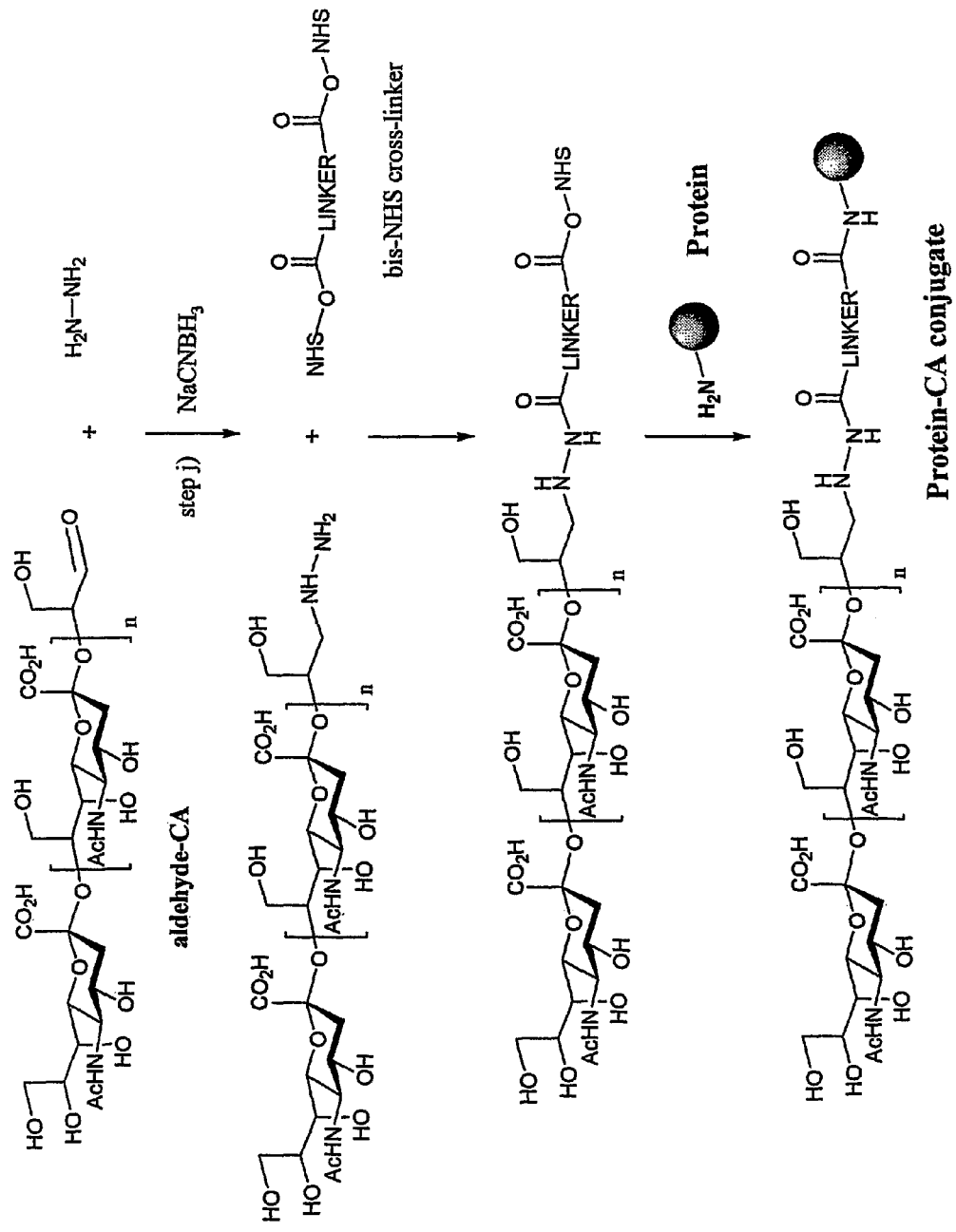
Figure 8a: Preparation of CA-protein conjugates via NHS on reducing end

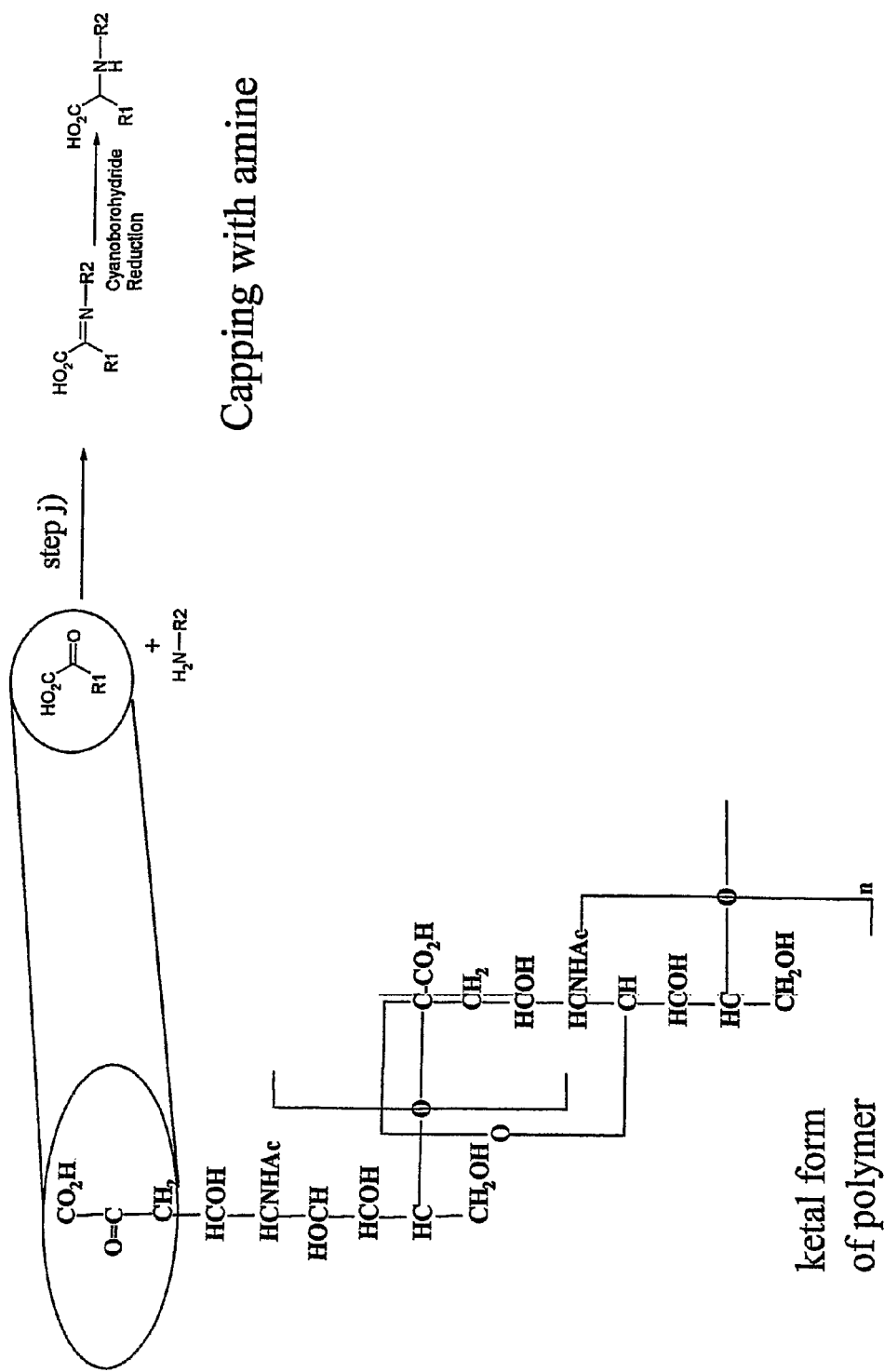
Figure 8b: Capping of reducing end of polysialic acid

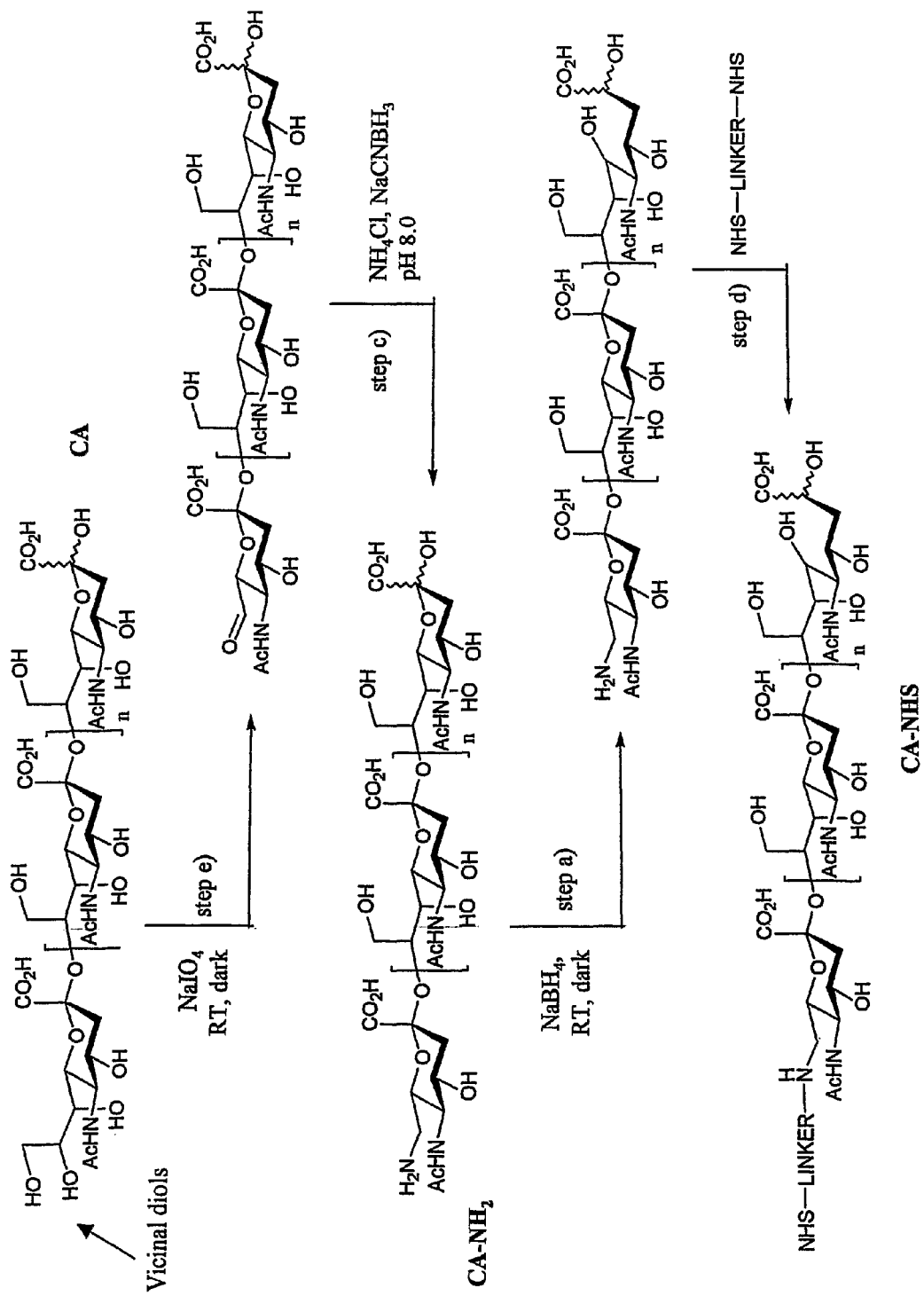
Figure 8c: Preparation of non-reducing end derivatised CA

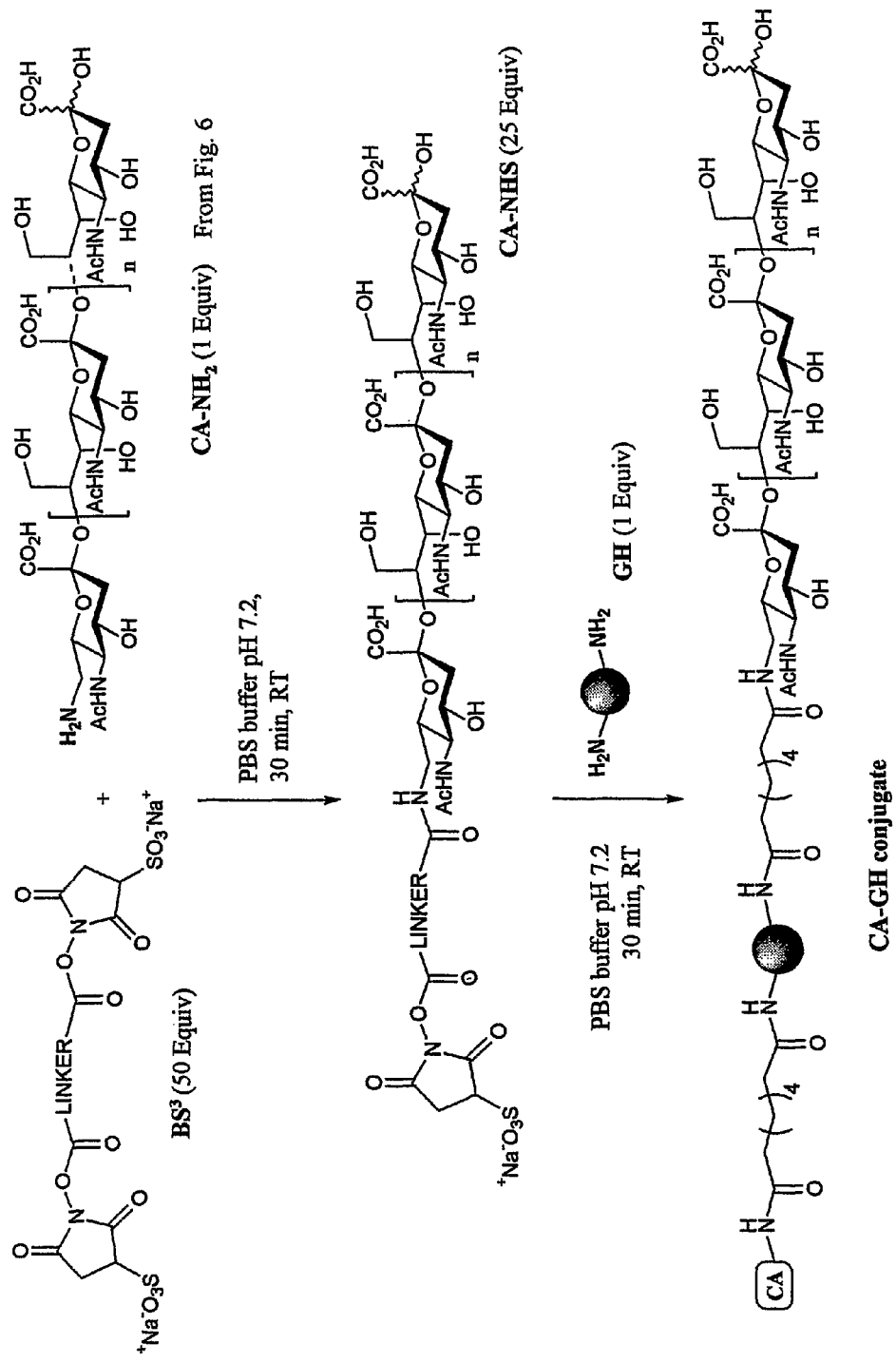
Figure 9: Preparation of CA-protein conjugates using BS³ on non-reducing end

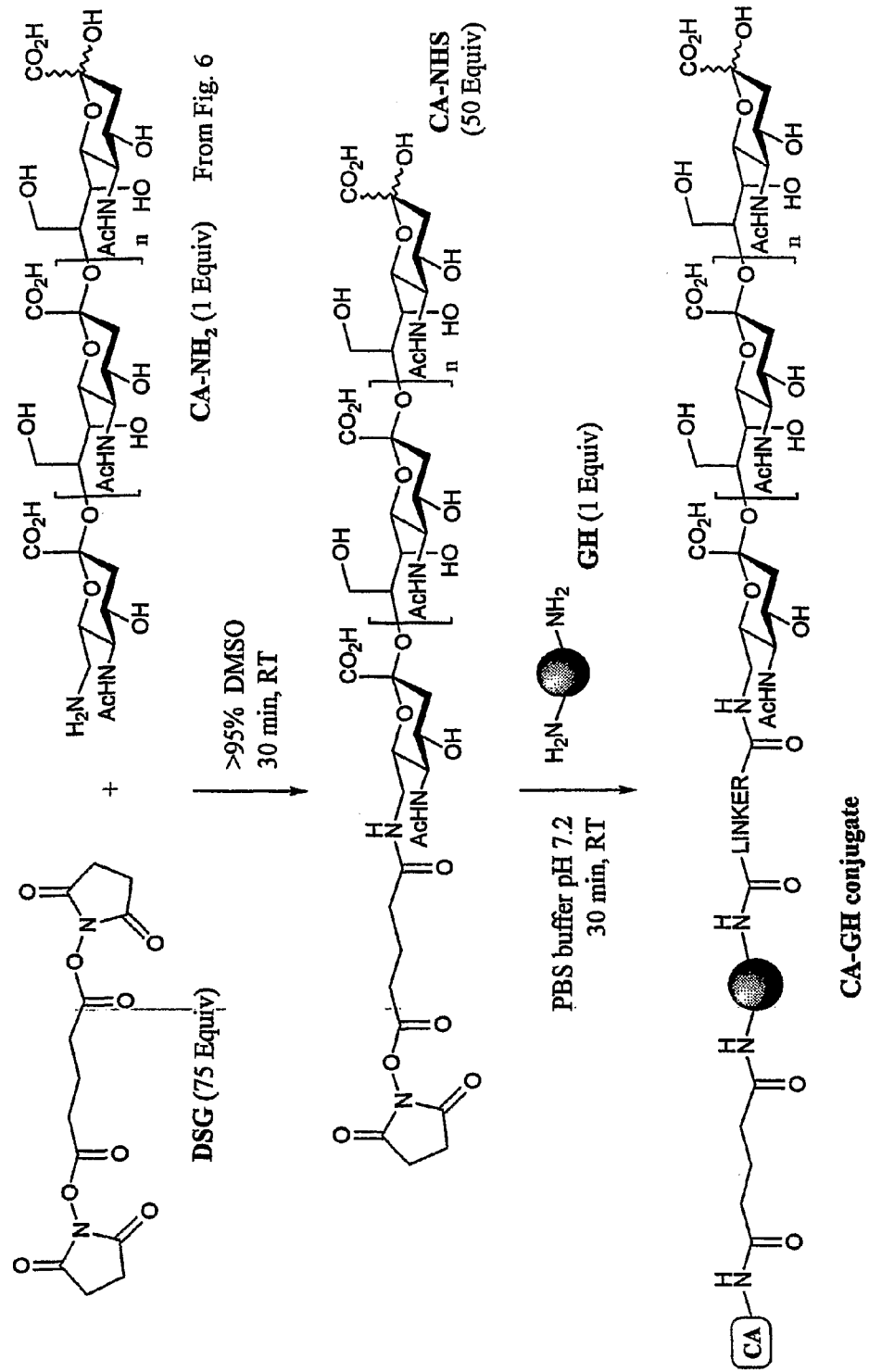
Figure 10: Preparation of CA-protein conjugates using DSG on non-reducing end

Figure 11: GPC of reacted and unreacted CA-NH₂ samples
RI scan on GPC of 35kDa CA-NH₂ reacted with BS³
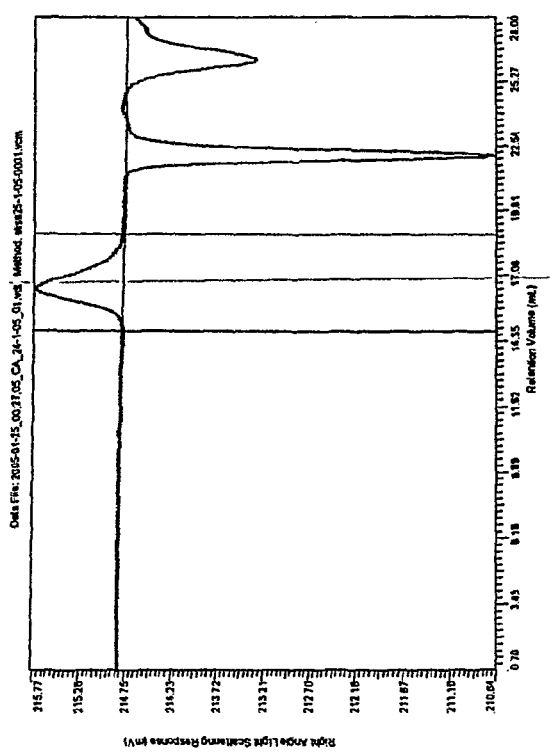
RI scan on GPC of unreacted 35kDa CA-NH₂
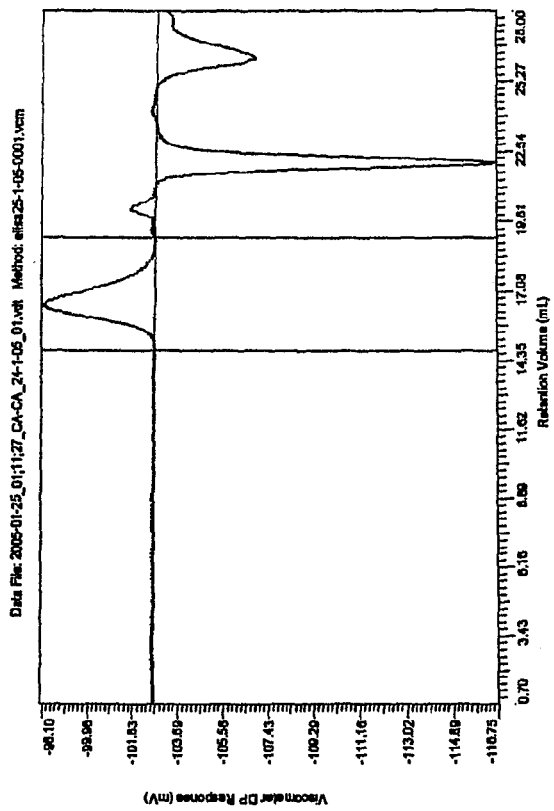

Figure 12: Size-exclusion HPLC on CA-NHS-GH conjugation reactions
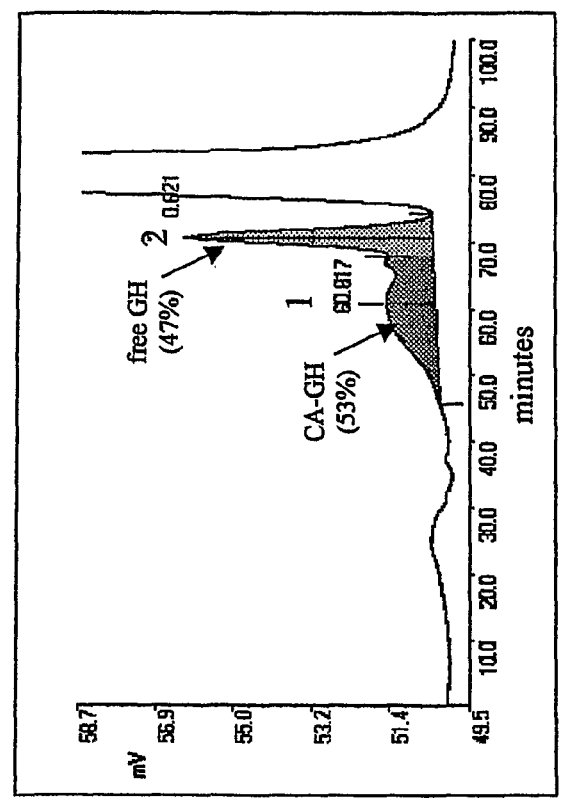
Conjugation using BS³ – 53% conjugation
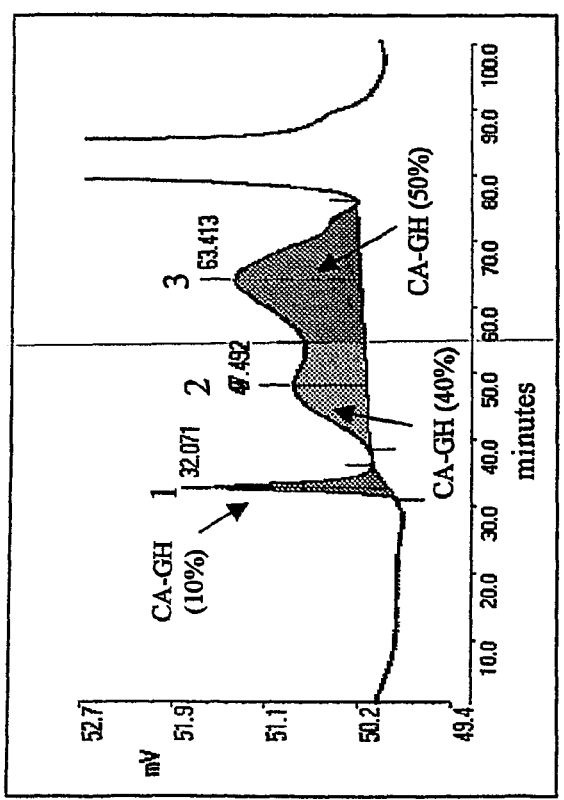
Conjugation using DSG – 100% conjugation
Eluent: 0.15M ammonium bicarbonate, rate: 0.25 mL/min using superose 6 column

Figure 13: SDS-page of GH and GH-colominic acid conjugates
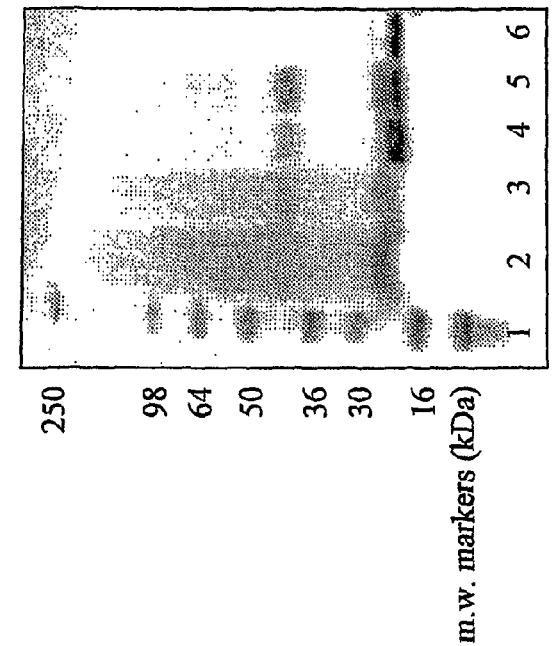
Conjugation using 50 equiv BS³
1) Markers
2) CA-NHS-GH (reaction mixture)
3) CA-NHS-GH (reaction mixture)
4) GH reacted with BS³
5) GH reacted with BS³
6) Native GH
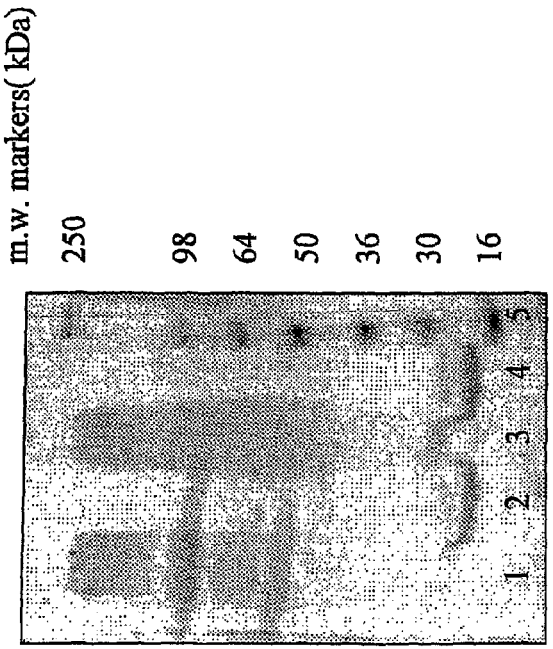
Conjugation using 75 equiv of BS³ and DSG
1) CA-NHS-GH (reaction mixture for BS³)
2) Native GH
3) CA-NHS-GH (reaction mixture for DSG)
4) Native GH
5) Markers

Figure 14: Native-PAGE of different CAs
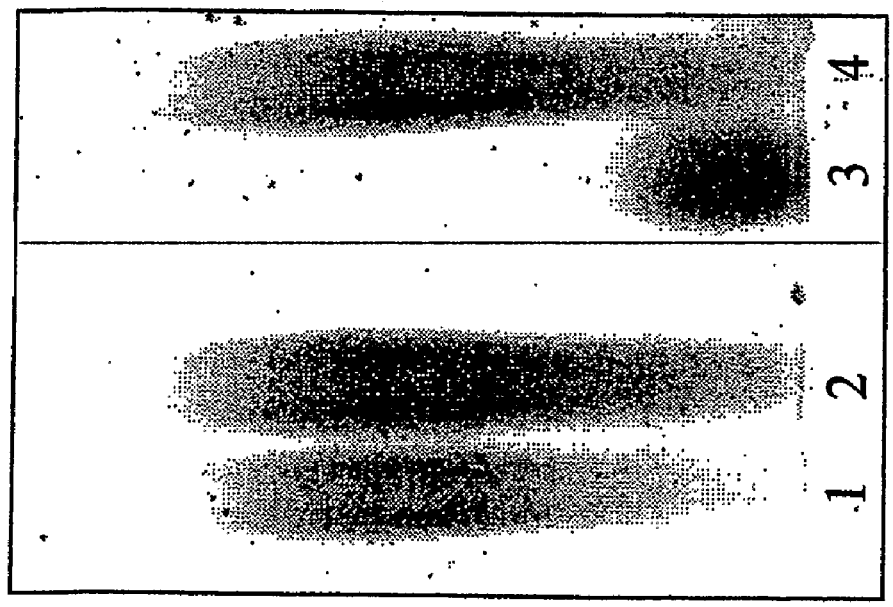
1) CA-NH$_2$ (35kDa) reaction with BS$^3$
2) CA-NH$_2$ (35kDa) reaction with BS$^3$
3) CA (5kDa) standard
4) CA (35kDa) standard

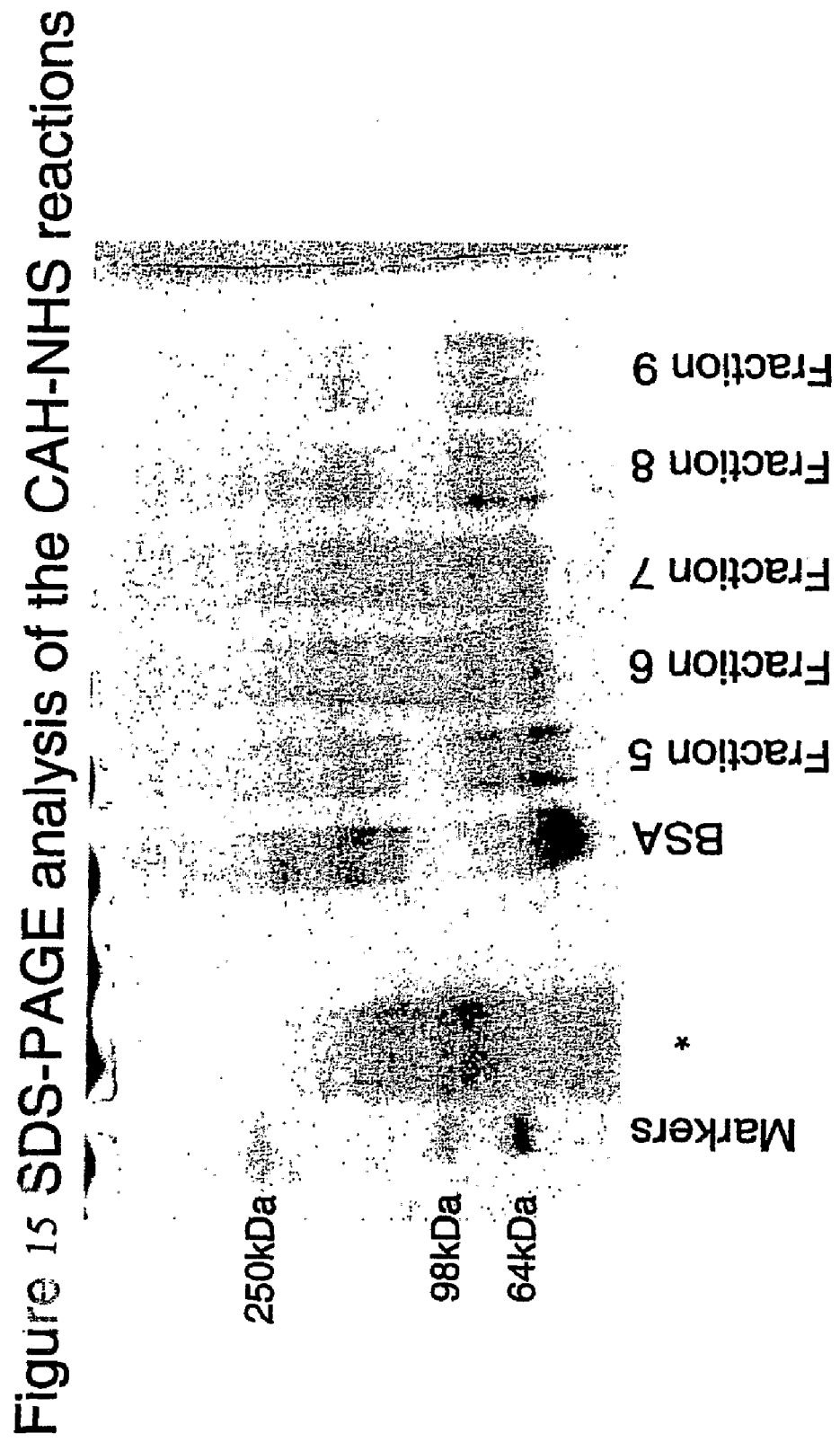
Figure 15 SDS-PAGE analysis of the CAH-NHS reactions

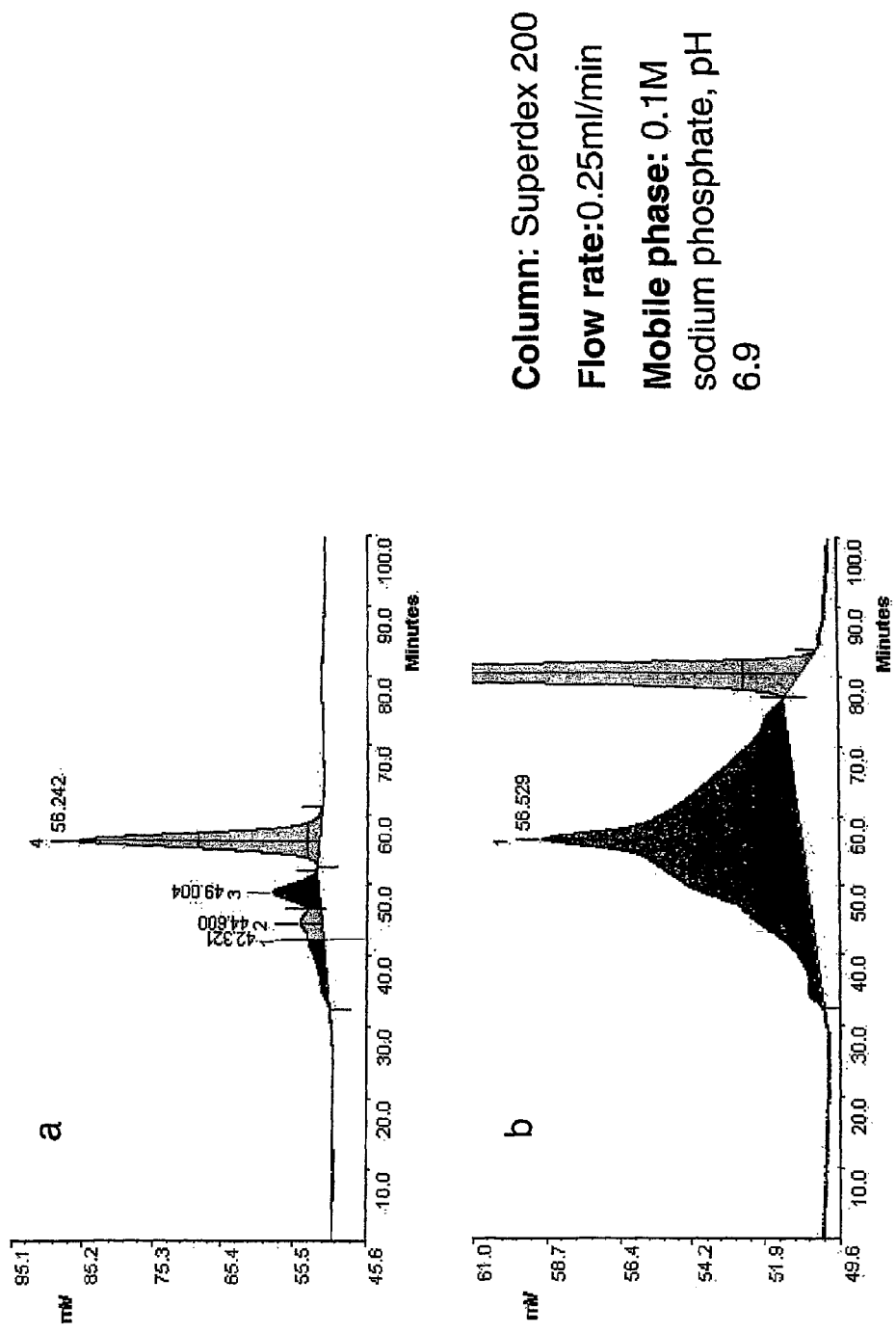
Figure 16 Size exclusion chromatography analysis

ACTIVATED SIALIC ACID DERIVATIVES FOR PROTEIN DERIVATISATION AND CONJUGATION

CROSS-REFERENCE TO RELATED APPLICATIONS

This application is the national phase of PCT application PCT/GB06/000540 having an international filing date of 16 Feb. 2006, which claims priority from European Application No. 05251017.9 filed 23 Feb. 2005, and from PCT application PCT/GB05/003160 filed 12 Aug. 2005. The contents of the above applications are incorporated by reference herein in their entirety.

The present invention relates to derivatives of compounds such as polysialic acids, which have terminal sialic acid units, and preferably consisting essentially of only sialic acid units, having an N-hydroxysuccinimide (NHS) group for reaction with substrates at the reducing or non-reducing end and to methods of producing them. The derivatives are useful for conjugation to amine-group containing substrates such as peptides, proteins, drugs, drug delivery systems (e.g. liposomes), viruses, cells (e.g. animal cells), microbes, synthetic polymers or copolymers etc.

Polysialic acids (PSAs) are naturally occurring unbranched polymers of sialic acid produced by certain bacterial strains and in mammals in certain cells [Roth et. al., 1993]. They can be produced in various degrees of polymerisation: from n=about 80 or more sialic acid residues down to n=2 by either limited acid hydrolysis, digestion with neuraminidases or by fractionation of the natural, bacterially or cell derived forms of the polymer. The composition of different PSAs also varies such that there are homopolymeric forms i.e. the alpha-2,8-linked PSA comprising the capsular polysaccharide of E. coli strain K1 and of the group-B meningococci, which is also found on the embryonic form of the neuronal cell adhesion molecule (N-CAM). Heteropolymeric forms also exist, such as the alternating alpha-2,8 alpha-2,9 linked PSA of E. coli strain K92 and the group C polysaccharides of N. meningitidis. In addition, sialic acid may also be found in alternating copolymers with monomers other than sialic acid such as group W135 or group Y of N. meningitidis. PSAs have important biological functions including the evasion of the immune and complement systems by pathogenic bacteria and the regulation of glial adhesiveness of immature neurons during foetal development (wherein the polymer has an anti-adhesive function) [Muhlenhoff et. al., 1998; Rutishauser, 1989; Troy, 1990, 1992; Cho and Troy, 1994], although there are no known receptors for PSAs in mammals. The alpha-2,8-linked PSA of E. coli strain K1 is also known as 'colominic acid' and is used (in various lengths) to exemplify the present invention.

The alpha-2,8 linked form of PSA, among bacterial polysaccharides, is uniquely non-immunogenic (eliciting neither T-cell nor antibody responses in mammalian subjects) even when conjugated to immunogenic carrier protein, which may reflect its existence as a mammalian (as well as a bacterial) polymer. Shorter forms of the polymer (up to n=4) are found on cell-surface gangliosides, which are widely distributed in the body, and are believed to effectively impose and maintain immunological tolerance to PSA. In recent years, the biological properties of PSAs, particularly those of the alpha-2,8 linked homopolymeric PSA, have been exploited to modify the pharmacokinetic properties of protein and low molecular weight drug molecules [Gregoriadis, 2001; Jain et. al., 2003; U.S. Pat. No. 5,846,951; WO-A-0187922]. PSA derivatisation of a number of therapeutic proteins including catalase and asparaginase [Fernandes and Gregoriadis, 1996 and 1997] gives rise to dramatic improvements in circulation half-life and their stability and also allows such proteins to be used in the face of pre-existing antibodies raised as an undesirable (and sometimes inevitable) consequence of prior exposure to the therapeutic protein [Fernandes and Gregoriadis, 2001]. In many respects, the modified properties of polysialylated proteins are comparable to proteins derivatised with polyethylene glycol (PEG). For example, in each case, half-lives are increased, and proteins and peptides are more stable to proteolytic digestion, but retention of biological activity appears to be greater with PSA than with PEG [Hreczuk-Hirst et. al., 2002]. Also, there are questions about the use of PEG with therapeutic agents that have to be administered chronically, as PEG is only very slowly biodegradable [Beranova et. al., 2000] and both high and low molecular weight forms tend to accumulate in the tissues [Bendele, et. al., 1998; Convers, et. al., 1997]. PEGylated proteins have been found to generate anti PEG antibodies that could also influence the residence time of the conjugate in the blood circulation [Cheng et. al., 1990]. Despite, the established history of PEG as a parenterally administered polymer conjugated to therapeutics, a better understanding of its immunotoxicology, pharmacology and metabolism will be required [Hunter and Moghimi, 2002; Brocchini, 2003]. Likewise there are concerns about the utility of PEG in therapeutic agents that require high dosages, (and hence ultimately high dosages of PEG), since accumulation of PEG may lead to toxicity. The alpha 2,8 linked PSA therefore offers an attractive alternative to PEG, being an immunologically 'invisible' biodegradable polymer which is naturally part of the human body, and that can degrade, via tissue neuraminidases, to sialic acid, a non-toxic saccharide.

Our group has described, in previous scientific papers and in granted patents, the utility of natural PSAs in improving the pharmacokinetic properties of protein therapeutics [Gregoriadis, 2001; Fernandes and Gregoriadis, 1996, 1997, 2001; Gregoriadis et. al., 1993, 1998, 2000; Hreczuk-Hirst et. al., 2002; Mital, 2004; Jain et. al., 2003, 2004; U.S. Pat. No. 5,846,951; WO-A-0187922[. Now, we describe new derivatives of PSAs, which allow new compositions and methods of production of PSA-derivatised proteins (and other forms of therapeutic agents). These new materials and methods are particularly suitable for the production of PSA-derivatised therapeutic agents intended for use in humans and animals, where the chemical and molecular definition of drug entities is of major importance because of the safety requirements of medical ethics and of the regulatory authorities (e.g. FDA, EMEA).

Methods have been described previously for the attachment of polysaccharides to therapeutic agents such as proteins [Jennings and Lugowski, 1981; U.S. Pat. No. 5,846,951; WO-A-0187922]. Some of these methods depend upon chemical derivatisation of the 'non-reducing' end of the polymer to create a protein-reactive aldehyde moiety (FIG. 1). The reducing end of PSA (and other polysaccharides) is only weakly reactive with proteins under the mild conditions necessary to preserve protein conformation and the chemical integrity of PSA during conjugation. The non-reducing end of sialic acid terminal unit, which contains vicinal diols, can be readily (and selectively) oxidised with periodate to yield a mono-aldehyde derivative. This derivative is much more reactive towards proteins and comprises of a suitably reactive element for the attachment of proteins via reductive amination and other chemistries. We have described this previously in U.S. Pat. No. 5,846,951 and WO-A-0187922. The reaction is illustrated in FIG. 1 in which;

a) shows the reaction of the aldehyde with a primary amine group of a protein after the oxidation of CA (alpha-2,8 linked PSA from *E. coli*) with sodium periodate to form a protein-reactive aldehyde at the non-reducing end of the terminal sialic acid and b) shows the selective reduction of the Schiff's base with sodium cyanoborohydride (NaCNBH$_3$) to form a stable irreversible covalent bond with the protein amino group.

In WO2005/016973 we describe polysaccharide derivatives which have a sulfhydryl-reactive group introduced via a terminal sialic acid unit. This unit is usually introduced by derivatisation of a sialic acid unit at the non-reducing end of the polysaccharide. The sulfhydryl reactive group is preferably a maleimido group. The reaction to introduce this group may involve reacting a heterobifunctional reagent having a sulfhydryl-reactive group at one end and a group such as a hydrazide or an ester at the other end with an aldehyde or amine group on the sialic acid derived terminal unit of the polysaccharide. The product is useful for site specific derivatisation of proteins, e.g. at Cys units or introduced sulfhydryl groups.

Although the various methods that have been described to attach PSAs to therapeutic agents [U.S. Pat. No. 5,846,951; WO-A-0187922], are theoretically useful, achievement of acceptable yields of conjugate via reaction of proteins with the non-reducing end (aldehyde form) of the PSA requires reaction times that are not conducive to protein stability at higher temperature (e.g. interferon alpha-2b). Secondly, reactant concentrations (i.e. polymer excess) are required that may be unattainable or uneconomical.

Therefore, we have solved the above problems by developing a new method for conjugation of polysialic acids which have NHS-sialic acid groups at the reducing and/or non-reducing termini, to proteins. The weak reactivity of the reducing end can be exploited to beneficial effect (by destroying the non-reducing end, capping the reducing end and derivatising with a bifunctional crosslinker), thus avoiding the product complexity described in FIGS. 2 and 3 using the established method (FIG. 1) of reductive amination of proteins with periodate oxidised CA.

Jennings and Lugowski, in U.S. Pat. No. 4,356,170, describe derivatisation of bacterial polysaccharides with proteins via an activated reducing terminal unit involving a preliminary reduction step followed by an oxidation step. Examples where this approach has been employed by Jennings et al include polysaccharides wherein the reducing terminal unit is N-acetyl mannosamine, glucose, glucosamine, rhamnose and ribose.

In EP-A-0454898 an amino group of a protein is attached to an aldehyde group which has been synthesised by reducing and partially oxidising the reducing terminal sugar moiety of a glycosaminoglycan. The glycosaminoglycans treated in this way include hyaluronic acid, chondroitin sulphate, heparin, heparan sulphate, and dermatan sulphate. None of these compounds has a sialic acid unit at the reducing terminal.

In the invention there is provided a novel compound comprising a polysialic acid substrate having at least one of its terminal units derived from a sialic acid unit which includes an ester of N-hydroxysuccinimide linked to the terminal unit at either the 2 or 7-carbon, optionally via a linker. The N-succinimidyloxy group is hereinafter referred to as an NHS group. In this invention the succinimidyl moiety may be unsubstituted or substituted by groups such as sulphonyl or other groups to confer useful solubility properties. The derivatised terminal unit may be derived from a non-reducing terminal sialic acid group or from a reducing terminal sialic acid group. There may be two such NHS groups per PSA molecule, for instance one on a terminal unit derived from a non-reducing terminal sialic acid group and the other derived from a reducing terminal sialic acid group.

The compounds of the invention may also be defined in terms of general formulae. The novel compounds preferably have the general formula I, II or III

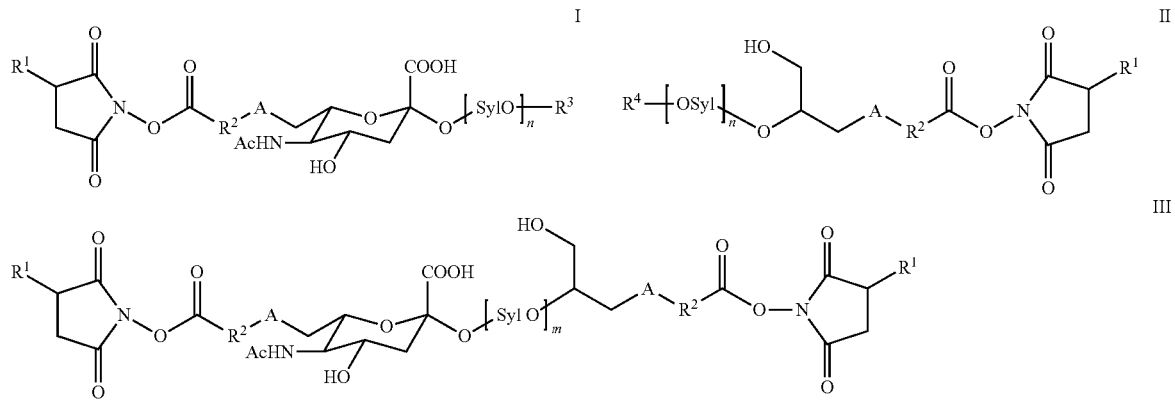

in which $R^1$ is H or sulfonyl;

$R^2$ is a linking group;

A is $NR^5$, $NR^5NR^6$, O or SR wherein $R^5$ and $R^6$ are independently selected from H, $C_{1-4}$ alkyl and aryl;

SylO is a sialyl group;

n is 1-100 and m is 0-100;

$R^3$ is hydrogen or a mono-, di-, oligo- or polysialic acid group, a protein, a peptide, a lipid, a drug, a component of a cell membrane or wall or a drug delivery system; and $R^4$ is hydrogen or a mono-, di-, oligo- or polysialic acid group, an alkyl group, an acyl group, a drug or a drug delivery system.

The linking group, $R^2$, together with the NHS group and ester linkage which are found in compounds I to III typically form a structure which is derived from the bifunctional NHS reagent used to synthesise the compounds. Suitable bifunctional reagents are listed later in the application. During the synthesis the group labelled as A which is derived from a PSA starting material attaches itself to the appropriate end of the bifunctional reagent with corresponding loss of a leaving group from the NHS reagent (at an opposite end to the NHS group which does not react), or alternatively structural rearrangement of the reagent. Typically, the linking group $R^2$ will comprise an alkane-diyl group together with a carbonyl to which A is attached in compounds of formula I to III. Preferably $R^2$ is $C_pH_{2p}CO$ where p is 2-12. Alternatively, the linking group may comprise an alkanediyl group wherein one of the alkane carbon atoms is attached to the A group. $R^2$ may include mid-chain ester, amide, ether, thioether and/or 1-thio-N-succinimidyl amine linkages for instance derived from preliminary derivatisation reactions of a PSA reagent or of an NHS reagent. $R^2$ may be an alkyleneoxyalkylene group or an alkyleneoligooxyalkylene group.

A is preferably $NR^5$, wherein $R^5$ is hydrogen, which is derived from a primary amine PSA starting reagent. Examples of such amine PSA derivatives and methods for producing them are given below.

In one embodiment the terminal sialic acid unit has been subjected to a preliminary chemical reaction to generate useful functional groups to which a maleimide-group containing reagent may be linked.

In one embodiment we have found it convenient to use the chemistry disclosed in our earlier publications in which an aldehyde group is generated, as a preliminary step to generate the functional group via which the NHS group may be linked.

The invention includes processes for forming the novel compounds. There is also provided a new process for synthesising the new compounds in which a PSA substrate is reacted, optionally after preliminary derivatisation step(s) of the terminal sialic acid unit(s), with a bifunctional reagent, one of the functionalities of which is an NHS ester and the other of the functionalities is reactive with a sialic acid unit(s) or derivative(s), thereof, as the case may be, under conditions such that covalent conjugation between the reagent and the 2 or 7 carbon atom from the terminal sialic acid group(s) or derivative thereof occurs and the NHS group remains unchanged.

In a preferred embodiment the sialic acid unit in the substrate is subjected to a preliminary step in which an amine group is generated.

Where the sialic acid unit which is derivatised is a reducing terminal unit the preliminary step may involve amination at the anomeric carbon, or, preferably, the following sequence of steps:
 a) reduction to open the ring of the reducing terminal sialic acid unit to form a vicinal diol group;
 b) selective oxidation of the vicinal diol group formed in step a) to form an aldehyde group;
 c) conversion of aldehyde in step b) to an amino group by reductive amination with an ammonium compound, e.g. using cyano borohydrate; and
 d) reacting the amino group from step c) with a homobifunctional NHS reagent in excess.

The starting substrate material having a reducing terminal sialic acid group used in this process should preferably have the sialic acid unit at the reducing terminal end joined to an adjacent unit through its eight carbon atom. In step b), after the reductive ring opening of the terminal sialic acid, the 6,7-diol group at the reducing end is oxidised to form an aldehyde group at the carbon 7 atom with subsequent introduction of amino (step c) and NHS (step d) group.

In an alternative embodiment, where the sialic acid unit at the reducing terminal end is joined to the adjacent unit through the 9 carbon atom, in step b) the C-7, C-8 diol group, at the reducing end, formed during step a) is oxidised to form an aldehyde group on the 8 carbon atom, followed by forming an amino group (step c) and then an NHS group (step d).

According to one preferred embodiment, the starting material is a PSA with a sialic acid at the reducing terminal, and also a terminal sialic acid unit at the non-reducing end which has a vicinal diol group. In the first step of the process (step a) a reduction reaction is performed at the reducing end of the polysaccharide to open up the ring to furnish a vicinal diol. During the reduction step the vicinal diol functionality at the non-reducing end is not modified and remains intact. The second step is oxidation (step b) and during this process the vicinal diols at the non-reducing and reducing ends will be oxidised to form aldehyde groups. In step c the aldehydes will be aminated and in step d the NHS groups will be attached. As a result the product will be bi-functional that is have two NHS groups and may have useful therapeutic activities derived from its ability to cross-link substrates via reaction with both NHS groups on the reducing and non-reducing end with suitably functionalised substrates.

According to another preferred embodiment of the process in which the reducing terminal sialic acid is aminated, a sialic acid starting substrate material also having a terminal sialic acid at a non-reducing terminal end is subjected to the following steps:
 e) a selective oxidation step to oxidise the non-reducing terminal sialic acid unit at the C-7, C-8 vicinal diol group to form a C-7-aldehyde; and
 f) a reduction step to reduce the C-7-aldehyde group to the corresponding alcohol. The step also simultaneously reductively opens the sialic acid ring on the reducing end i.e. takes place simultaneously with step a). This aspect of the invention provides sialic acid derivatives which have a 'passivated' sialic acid non-reducing terminal, allowing activation of the reducing terminal via periodate oxidation (step b) and reductive amination (step c).

According to a further embodiment of the invention there is provided a new process in which a sialic acid starting material having a terminal sialic acid at the non-reducing terminal end is subjected to the following: step e) a selective oxidation step to oxidise the non-reducing terminal sialic acid unit at the C-7, C-8 vicinal diol group to form an aldehyde on carbon atom 7; step c) conversion of aldehyde group from step e) to an amino group by reductive amination with an ammonium compound and; step d) modification of the resulting amino group.

The starting material used in this embodiment of the invention should preferably have the sialic acid unit at the non-reducing end joined to the adjacent unit through the adjacent unit's eight carbon atom. In step e) the C-7, C-8-diol group is oxidised to form an aldehyde group at carbon 7 atom, that is subsequently converted to an amino group (step c) and NHS group (step d).

In an alternative embodiment, where the sialic acid unit at the non-reducing terminal end is joined to the adjacent unit through the adjacent unit's 9 carbon atom, in step b) the C-7, C-8 diol of this adjacent group is oxidised to form an aldehyde group on the 8 carbon atom that is replaced with an amino group, (step c) and NHS group (step d).

The above-mentioned oxidation steps (b and e) should preferably be carried out under conditions such that there is substantially no mid-chain cleavage of a long-chain polymeric backbone starting material, and thus no substantial molecular weight reduction. Enzymes which are capable of carrying out this oxidation step may be used. More conveniently the oxidation is a chemical oxidation. The reaction may be carried out with immobilised reagents such as polymer-based perruthenate or with the more straightforward method using dissolved reagents. The oxidant is suitably perruthenate, or, preferably, periodate. Oxidation may be carried out with periodate at a concentration in the range of 1 mM to 1M, at a pH in the range 5 to 10, a temperature in the range 0 to 60° C. for a time in the range 1 min to 48 hours.

Suitable reduction conditions for steps a) and step f) may utilise hydrogen with catalysts or preferably hydrides, such as borohydrides. These may be immobilised as in Amberlite supported borohydride. Preferably alkali metal hydrides such as sodium borohydride is used as the reducing agent, at a concentration in the range 1 μM to 0.1 M, a pH in the range 6.5 to 10, a temperature in the range 0 to 60° C. and a period in the range 1 min to 48 hours. The reaction conditions are selected such that pendant carboxyl groups on the PSA starting material are not reduced. Where a preliminary oxidation step has been carried out (i.e at the non-reducing end) the aldehyde group generated is reduced to an alcohol group which is not part of a vicinal diol group. Other suitable reducing agents are cyanoborohydride under acidic conditions, e.g. polymer supported cyanoborohydride or alkali metal cyanoborohydride, L-ascorbic acid, sodium metabisulphite, L-selectride (trade mark), triacetoxyborohydride, etc.

During the various steps of reaction (e.g. reduction and oxidation), the respective intermediate must be isolated from oxidising and reducing agents, crosslinkers, and other reagents like $NaCNBH_3$, cystamine etc., prior to being subjected to subsequent steps. Where the steps are carried out in solution phase, isolation may be by conventional techniques such as expending excess oxidising agent using ethylene glycol, ethanol precipitation, dialysis of the polysaccharide, size exclusion chromatography and ultrafiltration to concentrate the aqueous solution. The product mixture from a reduction step again may be separated by dialysis and ultrafiltration. It may be possible to devise reactions carried out on immobilised oxidising and reducing reagents rendering isolation of product straightforward.

In the process of the invention wherein an intermediate amine compound is produced and is then reacted with a bifunctional NHS reagent, since NHS groups are reactive with amine groups it is convenient to use a homobifunctional NHS reagent. Where the two NHS groups of such a reagent are equally reactive it will be essential to use a significant excess of the reagent in order to minimise the extend of cross-linking, that is of reaction of two molecules of amine intermediate with one molecule of di-NHS reagent. The reaction must also be carried out under conditions such that the second NHS group remains intact, and the reaction product must be separable from excess unreacted NHS reagent.

NHS groups are highly unstable in water. Thus the reaction conditions must minimise contact of the NHS reagent with water or other protic solvent. Preferably the reaction is carried out in dimethylsulfoxide (DMSO). It may be necessary for a small amount of water or other protic and polar solvent to be included in order to solubilise the substrate. The amount should be minimised, for instance kept below 10% of total solvent. It may be desirable to raise the temperature to optimise solubilisation of the reagents and accelerate the reaction, provided that this does not result in a chemical modification such as oxidation or cleavage of the substrate to an undesirable degree.

In a further embodiment an aldehyde terminated intermediate, produced according to steps a) and b) and/or step c) is reacted with hydrazine to form a hydrazone intermediate. The hydrazone groups are reactive with NHS groups. In the essential step of the process of the invention where a bifunctional NHS reagent is reacted, the NHS reagent is conveniently a di NHS compound. The same precautions must be observed as for reactions on amine intermediates described above. A reaction scheme is shown as scheme 8a).

Suitable di-NHS reagents are:
bis[2-succinimidyloxycarbonyl-oxy)ethyl]sulfone (BSOCOES) and its sulfo analog,
bis(sulfosuccinimidyl)suberate ($BS^3$),
disuccinimidyl glutarate (DSG),
dithiobis (succinimidyl propionate) (DSP),
disuccinimidyl suberate (DSS),
disuccinimidyl tartrate (DST) or its sulfo analog,
3,3'-dithiobis (sulfosuccinimidyl propionate) (DTSSP), and
ethylene glycol bis(succinimidyl succinate) (EGS) and its sulfo analog.

According to an alternative embodiment of the process, instead of a preliminary step involving formation of an amine group on the substrate, there is provided a preliminary step in which a thiol group is provided, preferably at one terminal sialic acid unit, or, alternatively at a terminal sialic acid unit and at the terminal unit at an opposite end, which may be a sialic acid or another sugar residue.

The thiol group is, for instance, formed by reacting cystamine with an aldehyde group followed by reduction. The aldehyde group may be introduced at one or both terminal units by carrying out steps a) and b) and/or step e) on a starting material with respective terminal groups. The starting material may additionally have a non-reducing terminal sugar with a vicinal diol group which may be converted to an aldehyde for reaction with cystamine. Alternatively such a terminal group may be deactivated by sequential oxidation then reduction steps to avoid formation of a difunctional thiol intermediate. The thiolation is conducted using the general procedure described by Pawlowski et al.

The thiol group may, alternatively be introduced in a series of steps carried out on the amine intermediate produced above in steps a-c. The thiol group is introduced by reaction of the amine group with a 2-iminothiolane (2-IT) (Pawlowski, A. et al op. cit) comprising a thiolated sialic acid unit.

A thiol group containing intermediate is a novel compound and represents a further aspect of the invention. The compound may be represented by the following general formulae IV, V, VI, or VII

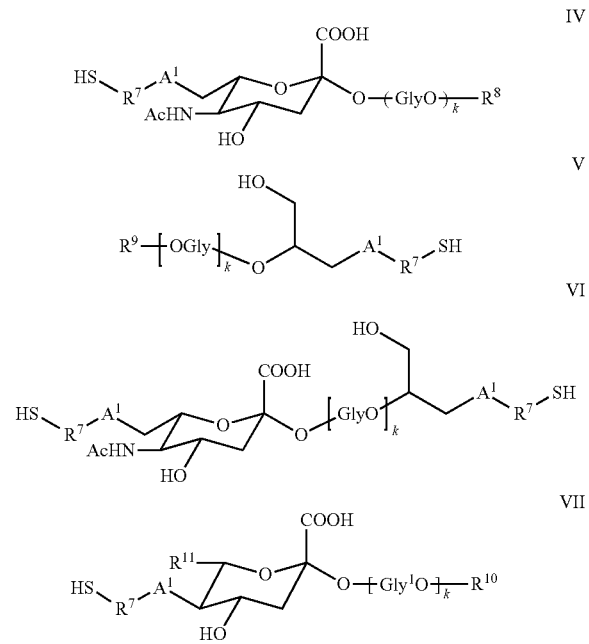

in which
R$^7$ is a linking group;
A$^1$ is NR$^{12}$ where R$^{12}$ is H, C$_{1-4}$ alkyl, or aryl;
GlyO is a glycosyl group and k is 0-100;
Gly$^1$O is a glycosyl group which is optionally derivatised on a pendant carboxylic acid group; R$^8$ is a mono-, di-, oligo- or polysaccharide group, a protein, a peptide, a lipid, a drug, a drug delivery system, or a component of a cell membrane or wall; and $R^8$ and $R^9$ are each hydrogen or a mono-, di- or oligosaccharide group, an alkyl group, an acyl group, a drug, a lipid or a drug delivery system;

$R^{10}$ is a mono-, di-, oligo- or polysaccharide group, a protein, a peptide, a lipid, a drug, a drug delivery system, a component of a cell membrane or wall or a group

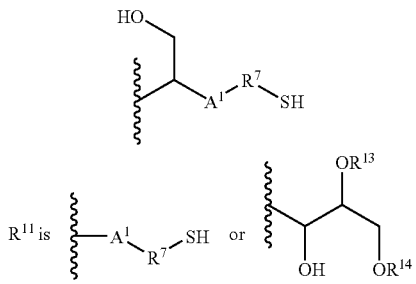

$R^{11}$ is wherein one of $R^{13}$ and $R^{14}$ is hydrogen and the other is a mono-di- or oligosaccharide group, an alkyl group, an acyl group, a drug, a lipid or a drug delivery system.

The linker group $R^7$ is selected from the same groups as $R^2$ listed above.

The definitions of $R^8$ and $R^9$ are preferably as disclosed above as preferred definitions for groups $R^3$ and $R^4$ respectively. GlyO is preferably SylO.

The thiol intermediate where GlyO is SylO is reacted in the essential step of the process of the first aspect of the invention with a heterobifunctional linker which has a thiol-reactive functional group as well as the NHS group. Such thiol-reactive groups are, for instance N-maleimido groups, or thiopyridyldithio groups, vinylsulphone or N-iodoacetamine groups. Examples of suitable bifunctional reagents are:

N-(α-maleimidoacetoxy)succinimide ester, (AMAS),
N-(β-maleimidopropyloxy)succinimide ester, (BMPS),
N-(ξ-maleimidocapryloxy)succinimide ester, (EMCS), or its sulfo analog,
N-(γ-maleimidobutyryloxy)succinimide ester, (GMBS), or its sulfo analog,
succinimidyl-4-(N-maleimidomethyl)-cyclohexane-1-carboxy-(6-amidocaproate) (LC-SMCC)
m-maleimido benzoyl-N-hydroxysuccinimide ester (MBS), or, its sulfo analog,
succinimidyl-4-(N-maleimidomethyl)-cyclohexane-1-carboxyate) (SHCC) or its sulfo analog,
succinimidyl-4-(p-maleimido phenyl) butyrate (SMPB) or its sulfo analog,
succinimidyl-6-(β-maleimido-propionamido) hexanoate (SMPH),
N-(k-maleimidoundecanoyloxy) sulfosuccinimide-ester (sulfo-KMUS),
succinimidyl 6-[3-2(2-pyridyldithio)-propionamido]hexanoate (LC-SPDP) or its sulfo analog,
4-succinimidyloxycarbonyl-methyl-a-(2-pyridyldithio) toluene (SMPT), or its sulfo-LC analog,
N-succinimidyl-3-(2-pyridyldithio)propionate (SPDP),
N-succinimidyl [4-vinylsulfonyl)benzoate (SVSB),
succinimidyl 3-(bromoacetamido)propionate (SBAP), and
N-succinimidyliodoacetate (SIA) and
N-succinimidyl(4-iodoacetyl)aminobenzoate (SIAB) or its sulfo analog.

Reaction conditions for the reactions generally used may also be used here, for instance with reference to Hermanson 1995.

The above-mentioned NHS heterobifunctional reagent may be selected depending on its water-solubility and whether the conjugate is to be cleavable or non-cleavable. The preference is for reagents with short and non-immunogenic linkers.

The reaction with the NHS-reagent is usually to be performed in 0-100% DMSO solutions (preferably with a minimum amount of water e.g. 10%) at a temperature between 0-150° C., preferably at 20° C. The sialic acid substrate on the intermediate may be dissolved by aid of heat e.g. sonication or microwave preferably under inert environment. Water-soluble NHS reagents can be used when the presence of organic solvents in subsequent uses of the product cannot be tolerated. In addition, water soluble NHS-reagent may be preferred where the use of the product is for cell surface conjugation as any unreacted reagent not removed from the product may not permeate the cell membrane.

In the invention the starting material is a polysialic acid (PSA). Such compounds may comprise units other than sialic acid in the molecule. For instance sialic acid units may alternate with other saccharide units. Preferably, however, the polysaccharide consists substantially only of units of sialic acid, which preferably are alpha-2,8 and/or alpha-2,9 linked (polysialic acid—hereinafter PSA).

The starting material has at least 2, preferably at least 5, more preferably at least 10, for instance at least 50, sialic acid units. The PSA may be derived from any source, preferably a natural source such as a bacterial, e.g. *E. coli* K1 or K92, group B meningococci, or even cow's milk or N-CAM. The sialic acid polymer may be a heteropolymeric polymer such as group 135 or group V of *N. meningitidis*, or may be chemically synthesized. The PSA may be in the form of a salt or the free acid. It may be in a hydrolysed form, such that the molecular weight has been reduced following recovery from a bacterial source. The PSA may be material having a narrow or wide spread of molecular weights such as having a polydispersity of 1.01, indeed even as much as 2 or more. Preferably the polydispersity of molecular weight of PSA to be employed is less than 1.2.

A population of PSAs either in their native form, or as intermediates of the types described above, or the final products having a wide molecular weight distribution may be fractionated into fractions with lower polydispersities, i.e. into fractions with differing average molecular weights. Fractionation is preferably done by anion exchange chromatography, using for elution a suitable basic buffer. We have found a suitable anion exchange medium, namely a preparative medium such as a strong ion-exchange material based on activated agarose, having quaternary ammonium ion pendant groups (i.e. strong base). The elution buffer is non-reactive and is preferably volatile so that the desired product may be recovered from the base in each fraction by evaporation. Suitable examples are amines, such as triethanolamine. Recovery may be by freeze-drying for instance. The fractionation method is suitable for a PSA starting material as well other PSA derivatives. The technique may thus be applied before or after the essential process steps in this invention.

Preferably the process of fractionation is carried out on a population of ionisable which have a molecular weight (Mw) preferably higher than 5 kDa using ion-exchange chromatography (IEC) and using as elution buffer a base or acid which is preferably volatile. Preferably the PSA has carboxylic acid groups and the ion-exchange is anion exchange. Preferably the elution buffer contains an amine, such as triethanolamine, with recovery of PSAs preferably via freeze-drying the elution fractions.

The PSA-NHS compound of the invention may be used in a subsequent process for derivatising amines, e.g. of biologically useful compounds. Such reactions can be done preferably in phosphate, bicarbonate/carbonate, HEPES or borate buffers at concentrations preferably between 5-200 mM. Other buffers may also be used if they do not contain primary amines. HEPES, for example, can be used because it contains only tertiary amines. A large excess of Tris/Glycine at neutral to basic pH may be added at the end of the reaction to quench it. The reactions may be preferably performed between pH 7 and 9 at 4° C. to 20° C. for 30 minutes to 2 hours. The PSA-NHS compound may be used in a 2-50 fold molar excess to protein (or other derivatisable compound) depending on the concentration of the amine. Typically, the concentration of the PSA-NHS compound may preferably vary from 0.1-10 mM. The amine, e.g. protein concentration may preferably be kept around 10-100 μM because more dilute protein solution result in excessive hydrolysis of the NHS group of the PSA-NHS compound.

The product NHS compound is of particular value for derivatising amine group-containing proteins, in which the amine group is suitably the epsilon amine group of a lysine or the N-terminal amino group. The product is of particular value for derivatising protein or peptide therapeutically active agents, such as cytokines, growth hormones, enzymes, hormones and antibodies or their fragments. Alternatively, the process may be used to derivatise drug delivery systems, such as liposomes, for instance by reacting the NHS group with an amine group of a liposome forming component. Other drug delivery systems are described in U.S. Pat. No. 5,846,951. Other materials that may be derivatised include viruses, microbes, cells, including animal cells, and synthetic polymers or copolymers.

The invention also provides methods in which the new compounds are reacted with biologically relevant compounds, having derivatisable amine groups under conditions suitable for reaction of the NHS group with the amine group to form a covalent conjugate. The biologically relevant molecule is preferably a peptide or a protein and the amine group is on a side chain of a Lys unit or is at the N-terminal of the peptide or protein. The degree of derivatisation may be less than 1.0, but is preferably at least 1.0, for instance at least 1.5, that is each molecule of biologically active compound is conjugated to at least one PSA substrate moiety.

The derivatisation of proteins and drug delivery systems by reaction with the new PSA compounds, may result in increased half life, improved stability, reduced immunogenicity or antigencity, and/or control of solubility and hence bioavailability and pharmacokinetic properties, or may enhance the solubility of actives or the viscosity of solutions containing the derivatised active.

The new preferred monofunctional PSA-NHS is highly reactive and is more conducive to the synthesis and manufacture of a pharmaceutically acceptable product, since it avoids the considerable complexity which may be created by use of PSA forms with unmodified reducing ends (FIG. 2). Production of the new form of the polymer (FIG. 5) involves, selective oxidation (step e), preferably by periodate (see earlier section) to introduce an aldehyde function at the non-reducing end followed by reductive amination (step c) and condensation to form NHS functionality (step d). Unlike the prior art illustrated in FIG. 1 however, this aldehyde moiety may be destroyed by reduction (step a), for instance with borohydride. At the other end of the polymer, the borohydride reduction step also simultaneously locks open the ring structure of the reducing end, by reducing the hemiketal. This simultaneous reduction of the ketone to a hydroxyl moiety introduces a new diol functionality at the reducing end, which is now amenable to selective oxidation in the second oxidation step. When the natural polymer has been (successively) oxidised with periodate, reduced with borohydride, oxidised a second time with periodate and aminated and conjugated to form an NHS compound, a new polymer form is created, which is truly monofunctional, having a single reactive group (i.e. NHS group) only at the formerly reducing end (FIG. 5).

The scheme for protein reactivity by condensation of the various derivatives is described in FIGS. 9 and 10. The monofunctional PSA can give rise only to single-orientation attachment to proteins, with the non-reducing end outermost, and is incapable of inadvertently cross-linking proteins. This new scheme of reaction (FIG. 5) method elegantly avoids the need to purify away the intended product from the various unintended products (described in FIG. 2), which are completely avoided in this new reaction scheme.

The following is a brief description of the drawings.

FIG. 1a is a reaction scheme showing the prior art activation of the non-reducing sialic acid terminal unit;

FIG. 1b is a reaction scheme showing the prior art reductive amination of the aldehyde moiety of the product of reaction scheme 1a using a protein-amine moiety;

FIG. 3 is a reaction scheme showing the tautomerism between the ketal and ring-closed forms of the reducing terminal sialic acid unit of a PSA;

FIG. 4 shows the preparation of reducing end derivatised NHS colominic acid (when non-reducing end has no vicinal diol)

FIG. 5 shows the preparation of reducing end derivatised $NH_2$-CA colominic acid (vicinal diol removed at non-reducing end)

FIG. 6 shows the general scheme for preparation of CA-NHS-protein conjugation

FIG. 7a shows the preparation of derivatised thiol colominic acid (CA-SH at non-reducing end)

FIG. 7b shows schematic representation of CA-protein conjugation via CA-SH using NHS-maleimide FIG. 7c shows the preparation of CA-protein conjugates via CA-SH using NHS-maleimide (AMAS)

FIG. 8a shows the preparation of CA-protein conjugates via NHS on reducing end

FIG. 8b shows capping of reducing end of polysialic acid

FIG. 8c shows preparation of non-reducing end derivatised CA

FIG. 9 shows the preparation of CA-protein conjugates using bis(sulfosuccinimidyl)suberate ($BS^3$) on non-reducing end FIG. 10 shows the schematic representation of CA-protein conjugation using the crosslinker DSG FIG. 11 shows gel permeation chromatography (GPC) chromatograms for CAs separated as in example 5.

FIG. 12 shows size exclusion HPLC on CA-NHS-growth hormone (GH) protein conjugation reactions (CA 35 kDa)

FIG. 13 shows the sodium dodecyl sulphate (SDS)-polyacrylamide gel electrophoresis (PAGE) of CA-NHS-GH conjugates (CA 35 kDa)

FIG. 14 shows native PAGE of unreacted and reacted CAs

FIG. 15 shows the SDS-PAGE analysis of the CAH-NHS reactions as in example 10

FIG. 16 shows the HPLC chromatogram of fraction 6 from FIG. 15.

EXAMPLES

Materials

Figure 2:
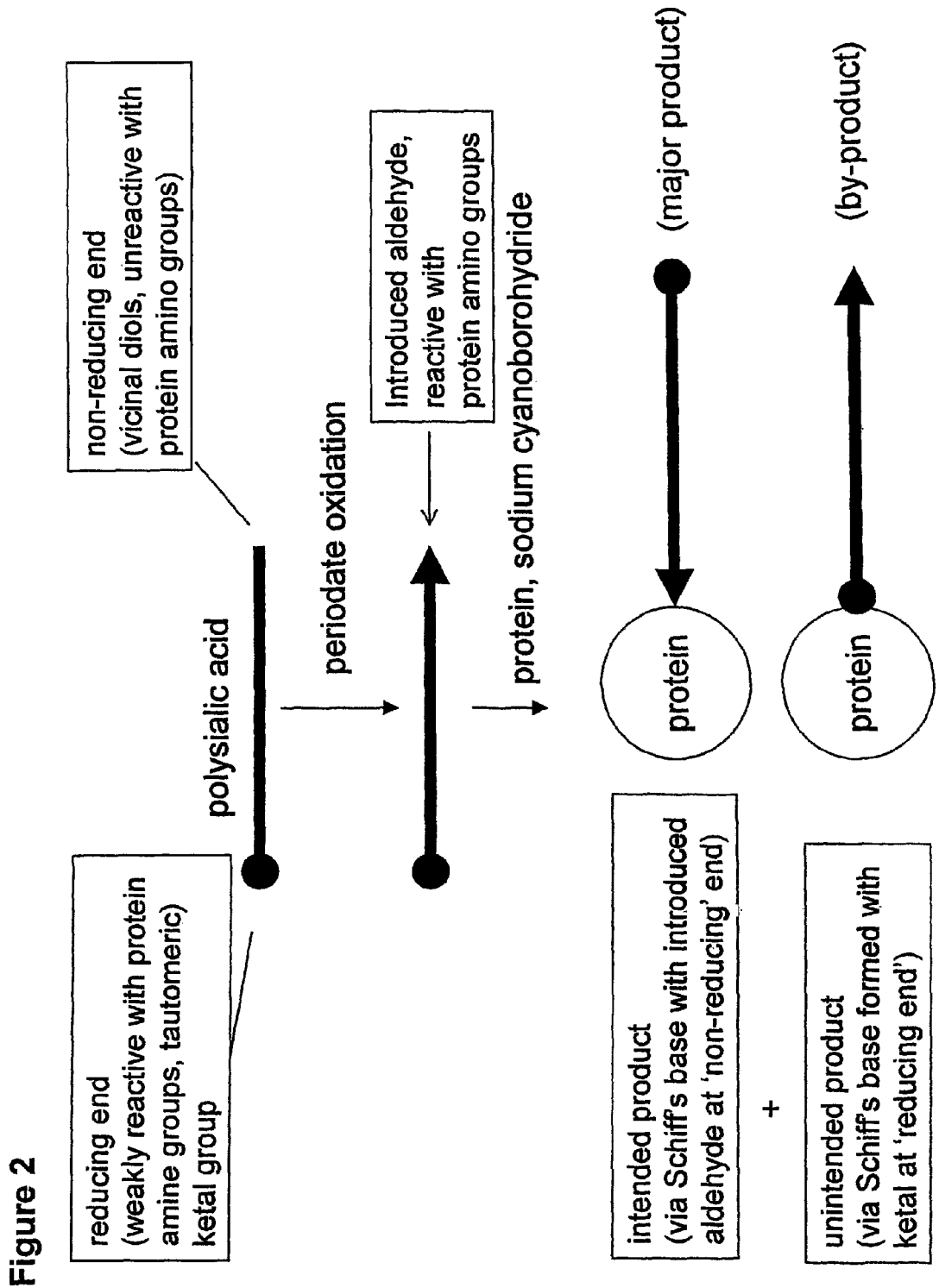
FIG. 2 represents schematically the potential by-products of the side reactions.

Sodium meta-periodate and molecular weight markers were obtained from Sigma Chemical Laboratory, UK. The CAs used, linear alpha-(2,8)-linked E. coli K1 PSAs (22.7 kDa average, polydispersity (p.d.) 1.34; 39 kDa p.d. 1.4; 11 kDa, p.d. 1.27) were from Camida, Ireland. Other materials included 2,4 dinitrophenyl hydrazine (Aldrich Chemical Company, UK), dialysis tubing (3.5 kDa and 10 kDa cut off limits (Medicell International Limited, UK); Sepharose SP HiTrap, PD-10 columns (Pharmacia, UK); XK50 column and Sepharose Q FF (Amersham Biosciences UK); Tris-glycine polyacrylamide gels (4-20% and 16%), Tris-glycine sodium dodecylsulphate running buffer and loading buffer (Novex, UK). Deionised water was obtained from an Elgastat Option 4 water purification unit (Elga Limited, UK). All reagents used were of analytical grade. A plate reader (Dynex Technologies, UK) was used for spectrophotometric determinations in protein or CA assays.

Methods

Protein and CA Determination

Quantitative estimation of CAs, as sialic acid, was carried out by the resorcinol method [Svennerholm 1957] as described elsewhere [Gregoriadis et. al., 1993; Fernandes and Gregoriadis, 1996, 1997]. GH was measured by the bicinchoninic acid (BCA) colorimetric method.

Example 1

Fractionation of CA by IEC (CA, 22.7 KDa, pd 1.34) [Reference]

An XK50 column was packed with 900 ml Sepharose Q FF and equilibrated with 3 column volumes of wash buffer (20 mM triethanolamine; pH 7.4) at a flow rate of 50 ml/min. CA (25 grams in 200 ml wash buffer) was loaded on column at 50 ml/min via a syringe port. This was followed by washing the column with 1.5 column volumes (1350 ml) of washing buffer.

The bound CA was eluted with 1.5 column volumes of different elution buffers (Triethanolamine buffer, 20 mM pH 7.4, with 0 mM to 475 mM NaCl in 25 mM NaCl steps) and finally with 1000 mM NaCl in the same buffer to remove all residual CA and other residues (if any).

The samples were concentrated to 20 ml by high pressure ultra filtration over a 5 kDa membrane (Vivascience, UK). These samples were buffer exchanged into deionised water by repeated ultra filtration at 4° C. The samples were analysed for average molecular weight and other parameters by GPC) (as reported in example 5) and native PAGE (stained with alcian blue; example 8). Narrow fractions of CA produced using above procedure were oxidised with sodium periodate and analysed by GPC and native PAGE for gross alteration to the polymer.

Example 2

Activation of CA [Reference]

Freshly prepared 0.02 M sodium metaperiodate (NaIO$_4$; 6 fold molar excess over CA) solution was mixed with CA at 20° C. and the reaction mixture was stirred magnetically for 15 min in the dark. The oxidised CA was precipitated with 70% (final concentration) ethanol and by centrifuging the mixture at 3000 g for 20 minutes. The supernatant was removed and the pellet was dissolved in a minimum quantity of deionised water. The CA was again precipitated with 70% ethanol and then centrifuged at 12,000 g. The pellet was dissolved in a minimum quantity of water, lyophilized and stored at −20° C. until further use.

Example 3

Determination of the Oxidation State of CA and Derivatives [Reference]

Quantitative estimation of the degree of CA oxidation was carried out with 2,4 dinitrophenylhydrazine (2,4-DNPH), which yields sparingly soluble 2,4 dinitrophenyl-hydrazones on interaction with carbonyl compounds. Non-oxidised CA and oxidised CA (CAO) (5 mg each) were added to the 2,4-DNPH reagent (1.0 ml), the solutions were shaken and then allowed to stand at 37° C. until a crystalline precipitate was observed [Shriner et. al., 1980]. The degree (quantitative) of CA oxidation was measured with a method [Park and Johnson, 1949] based on the reduction of ferricyanide ions in alkaline solution to ferric ferrocyanide (Persian blue), which is then measured at 630 nm. In this instance, glucose was used as a standard.

Example 4a

Preparation of Amino Colominic Acid (CA-NH$_2$) [Reference]

CAO at 10-100 mg/ml was dissolved in 2 ml of deionised water with a 300-fold molar excess of NH$_4$Cl, in a 50 ml tube and then NaCNBH$_4$ (5 M stock in 1 N NaOH(aq), was added at a final concentration of 5 mg/ml. The mixture was incubated at room temperature for 5 days. A control reaction was also set up with colominic acid instead of CAO. Product colominic acid amine derivative was precipitated by the addition of 5 ml ice-cold ethanol. The precipitate was recovered by centrifugation at 4000 rpm, 30 minutes, room temperature in a benchtop centrifuge. The pellet was retained and resuspended in 2 ml of deionised water, then precipitated again with 5 ml of ice-cold ethanol in a 10 ml ultracentrifuge tube. The precipitate was collected by centrifugation at 30,000 rpm for 30 minutes at room temperature. The pellet was again resuspended in 2 ml of deionised water and freeze-dried.

Example 4b

Assay for Amine Content

The TNBS (picryisulphonic acid, i.e. 2,4,6-tri-nitro-benzene sulphonic acid) assay was used to determine the amount of amino groups present in the product [Satake et. al., 1960].

In the well of a microtitre plate TNBS (0.5 µl of 15 mM TNBS) was added to 90 µl of 0.1 M borate buffer pH 9.5. To this was added 10 µl of a 50 mg/ml solution of CA-amine. The plate was allowed to stand for 20 minutes at room temperature, before reading the absorbance at 405 nm. Glycine was used as a standard, at a concentration range of 0.1 to 1 mM. TNBS trinitrophenylates primary amine groups. The TNP adduct of the amine is detected.

Testing the product purified with a double cold-ethanol precipitation using the TNBS assay showed close to 85% conversion.

Example 4c

Preparation of Colominic Acid-SH

Oxidised CA was derivatised with cystamine by reductive amination as described in example 4a, except using a 100-fold molar excess of cystamine instead of $NH_4Cl$. Before purifying the product, it was treated with 50 mM DTT at 37° C. for 1 h. The reduced product was purified by double ethanol precipitation and size exclusion chromatography on sepharose G25.

In another example, $CANH_2$ prepared as in example 4a, is dissolved in 10 mM PBS with 1 mM EDTA pH 8.0. A 50-fold molar excess of 2-iminothiolane is added and the reaction allowed to proceed for 1 h at 25° C. Unreacted 2-iminothiolate is removed by gel filtration on a sephadex G25 column equilibrated with the reaction buffer.

Thiol content is estimated using the Ellman's assay. Briefly 15 ul of sample are mixed with 150 ul of 0.1M phosphate, 1 mM EDTA, pH8 containing 0.08 mg/ml 5,5'-dithiobis(2-nitrobenzoic acid) (DTNB) and allowed to react for 30 minutes at room temperature and read at 405 nm. The product is suitable for reaction according to the schemes in FIGS. 7b and 7c.

Further, the thiol content of the polymer was found to be 60%.

Example 4d

Preparation of CA-NHS $CA-NH_2$ (35 kDa) (15-20 mg) synthesised in Reference Example 4a above was dissolved in 0.15M PBS (350 μL, pH 7.2) and then either 50 or 75 molar equivalents of $BS^3$ in PBS (150 μL, PH 7.2) was added. The mixture was vortexed for 5 seconds and then reacted for 30 minutes at 20° C. The CA-NHS product was purified by PD-10 column using PBS as eluent (pH 7.2) and used immediately for site-specific conjugation to the $NH_2$ groups in proteins and peptides. Determination of the CA concentration from the PD 10 fractions was achieved by analysing the sialic acid content using the resorcinol assay. The NHS content on the CA polymer was measured by UV spectroscopy by analysing the CA and NHS reaction solution at 260 nm and also by thin layer chromatography with visualization at 254 nm.

$CA-NH_2$ (35 kDa) (15-20 mg) synthesised in Example 4a above was either dissolved in the minimum amount of water (50-65 μL) to which was added DMSO (300-285 μL) or in >95% DMSO (350 μL) with the aid of heat (100-125° C.). 75 molar equivalents of DSG in DMSO (150 L) was added to the $CA-NH_2$ solution, vortexed for 5 seconds and then reacted for 30 minutes at 20° C. The CA-NHS product was purified either with dioxane precipitation (×2) or by PD-10 column using PBS as eluent (pH 7.2) and used immediately for site-specific conjugation to the $NH_2$ groups in proteins and peptides. As before determination of the CA concentration from the PD-10 fractions was measured using the resorcinol assay. The NHS content on the CA polymer was measured by UV spectroscopy (260 nm) and by thin layer chromatography (254 nm).

Example 5

Gel Permeation Chromatography of CA Samples [Reference]

CA (35 kDa) samples were dissolved in $NaNO_3$ (0.2M), $CH_3CN$ (10%, 5 mg/ml) and were chromatographed on 2×$GMPW_{XL}$ columns with detection by refractive index (GPC system: VE1121 GPC solvent pump, VE3580 RI detector and collation with Trisec 3 software (Viscotek Europe Ltd). Samples (5 mg/ml) were filtered through 0.45 μm nylon membrane and run at 0.7 cm/min with 0.2M $NaNO_3$ and $CH_3CN$ (10%) as the mobile phase (FIG. 11).

Example 6

Preparation of CA-NHS-Protein Conjugates (Using $BS^3$ and DSG)

GH in sodium bicarbonate (23 mg/ml, pH 7.4) was covalently linked to CA-NHS (35 kDa), from example 4b using an excess of $BS^3$. The reaction was performed in 0.15 M PBS (pH 7.2; 1.5 ml) using a molar ratio of 25:1 or 50:1 of CA-NHS:GH for a period of 30 minutes at 20° C. Polysialylated GH was characterised by SDS-PAGE and the conjugation yield determined by HPLC-size exclusion chromatography. Controls included subjecting the native protein to the conjugation procedure using $BS^3$ in the absence of any CA-NHS. $CA-NH_2$ was also subjected to the conjugation procedure using $BS^3$ in the absence of native GH.

GH in sodium bicarbonate (pH 7.4) was covalently linked to CA-NHS (35 kDa), which was prepared as discussed in example 4b using an excess of DSG. The reaction was performed in 0.15 M PBS (pH 7.2; 1.5 ml) using a molar ratio of 50:1 of CA-NHS:GH for a period of 30 minutes at 20° C. Polysialylated GH was characterised by SDS-PAGE and the conjugation yield determined by HPLC-size exclusion chromatography. Controls included subjecting the native protein to the conjugation procedure using DSG in the absence of any CA-NHS.

Example 7

HPLC-SEC of CA-NHS-GH Conjugates

CA-GH conjugates were dissolved in ammonium bicarbonate buffer (0.2M; pH7) and were chromatographed on superose 6 column with detection by UV index (Agilent, 10/50 system, UK). Samples (1 mg/ml) were filtered over 0.45 μm nylon membrane 175 μl injected and run at 0.25 cm/min with ammonium bicarbonate buffer as the mobile phase (FIG. 12).

Example 8

SDS and Native PAGE of CAs and CA-GH Conjugates

SDS-PAGE (MiniGel, Vertical Gel Unit, model VGT 1, power supply model Consort E132; VWR, UK) was employed to detect changes in the molecular size of GH upon polysialylation. SDS-PAGE of GH and its conjugates (with CA-NHS) at 0 minutes (control) and 30 minutes samples from the reaction mixtures as well as a process control (non oxidised CA), was carried out using a 4-20% polyacrylamide gel. The samples were calibrated against a wide range of molecular weight markers (FIGS. 13 and 14).

Results

CA (22.7 kDa) and its derivatives were successfully fractionated into various narrow species with a polydispersity less than 1.1 with m.w. averages of up to 46 kDa with different % of populations. Table 2 shows the results of separating the 22.7 kDa material.

TABLE 2

Ion exchange chromatography of CA22.7(pd 1.3)

| Elution buffers (in 20 mM Triethanolamine buffer + mM NaCl, pH7.4) | M.W. | Pd | % Population |
|---|---|---|---|
| 325 mM | 12586 | 1.091 | 77.4% |
| 350 mM | 20884 | 1.037 | 3.2% |
| 375 mM | 25542 | 1.014 | 5.0% |
| 400 mM | 28408 | 1.024 | 4.4% |
| 425 mM* |  |  | 7.4% |
| 450 mM | 43760 | 1.032 | 2.3% |
| 475 mM | 42921 | 1.096 | 0.2% |

*Not done

This process was scalable from 1 ml to 900 ml of matrix with the fractionation profile almost identical at each scale (not all results shown).

The fractionation of larger polymer (CA, 39 kDa, pd 1.4) produced species up to 90 kDa. This process can successfully be used for the fractionation of even large batches of the polymer. The results show that the ion exchange fractions are narrowly dispersed. This is consistent with the GPC data.

All narrow fractions were successfully oxidised with 20 mM periodate and samples taken from different stages of the production process and analysed by GPC and native PAGE, which showed no change in the molecular weight and polydispersity.

CA, a PSA, is a linear alpha-2,8-linked homopolymer of N-acetylneuraminic acid (Neu5Ac) residues (FIG. 1a).

Quantitative measurement of the oxidation state of CA was performed by ferricyanide ion reduction in alkaline solution to ferrocyanide (Prussian Blue) [Park and Johnson, 1949] using glucose as a standard. The oxidized CA was found to have a nearly 100 mol % of apparent aldehyde content as compared to native polymer. The results of quantitative assay of CA intermediates in the oxidation process using ferricyanide were consistent with the results of qualitative tests performed with 2,4-DNPH which gave a faint yellow precipitate with the native CA, and intense orange colour with the aldehyde containing forms of the polymer, resulting in an intense orange precipitate after ten minutes of reaction at room temperature.

The integrity of the internal alpha-2,8 linked Neu5Ac residues post periodate and borohydride treatment was analysed by GPC and the chromatographs obtained for the oxidised (CAO), amino CA (CA-$NH_2$), CA-NHS materials were compared with that of native CA. It was found (FIG. 12) that all CAs exhibit almost identical elution profiles, with no evidence that the various steps give rise to significant fragmentation or crosslinking (in case of CA-NHS) of the polymer chain. The small peaks are indicative of buffer salts.

Formation of the CA-GH conjugates was analysed by SEC-HPLC and SDS-PAGE. For the conjugation reaction with DSG the SDS-PAGE showed that there was no free GH remaining and that the conjugation reaction had gone to completion. This was confirmed by SEC-HPLC, whereby the CA-GH conjugates were eluted before the expected elution time of the free GH (a peak for free GH was not observed). On the other hand, analysis by SDS-PAGE of the conjugation reaction of CA-$NH_2$ to GH using $BS^3$ showed the presence of free GH, which was confirmed by SEC-HPLC with an elution peak around 70 minutes for the free protein. In addition, the SEC-HPLC enable the degree of conjugation to be determined at 53%.

The results (FIG. 13) show that in the conjugate lanes there are shifts in the bands which typically indicates an increase in mass indicative of a polysialylated-GH in comparison to GH. Further, GH conjugates were separated into different species by SEC-HPLC.

Example 9

Preparation of Colominic Acid Hydrazide (CAH) [Reference]

50 mg of oxidised colominic acid (19 kDa) was reacted with 2.6 mg of hydrazine (liquid) in 400 µl of 20 mM sodium acetate buffer, pH 5.5, for 2 h at 25° C. The colominic acid was then precipitated with 70% ethanol. The precipitate was redissolved in 350 µl phosphate buffer saline, pH 7.4 and $NaCNBH_3$ was added to 5 mg/ml. The mixture was allowed to react for 4 h at 25° C., then frozen overnight. $NaCNBH_3$ and reaction by products were removed by gel permeation chromatography on a PD10 column packed with Sephadex G25, using 0.15M $NH_4HCO_3$ as the mobile phase. The fractions (0.5 ml each) were analysed by the TNBS assay (specific to amino groups; described earlier). Fractions 6, 7, 8 and 9 (the void volume fractions) had a strong signal, well above the background. The background was high due to the presence of the $NH_4^+$ ions. Fractions 6, 7, 8 and 9 also contained colominic acid. These four fractions, were freeze-dried to recover the CA-hydrazide (CAH).

Example 10

Preparation of Colominic Acid NHS (CA-NHS) and Colominic Acid-Protein Conjugates 10 mg of 19 kDa CA-hydrazide were reacted with 9 mg of $BS^3$ in 400 µl of PBS (pH 7.4) for 30 minutes at room temperature. The reaction mixture was applied to a PD-10 column packed with Sephadex G25 collecting 0.5 ml fractions. 0.1 mg of BSA was added to each fraction between 5 and 9. After 2 hours at room temperatures the fractions reacted with BSA. These samples were analysed by SDS-PAGE and SEC HPLC.

These fractions have little colominic acid. The colominic acid rich fractions (6 and 7) have a protein streak in addition to the bands present in the other samples and BSA, which is clear evidence of conjugation (FIG. 15).

The HPLC chromatogram of fraction 6 shows that there is a big shift in the retention time for conjugate as compared to free protein confirming conjugation (FIGS. 16a and b).

The BSA used contains impurities. The BSA peak is at 56 minutes (FIG. 16a).

In addition to peak at 56 minutes, there are larger species which are conjugates. There is a large peak at 80 minutes, which is the NHS released from the CA-NHS as it reacts with the protein. This cannot be free $BS^3$ as the CAH was passed through a gel permeation chromatography column, which will have removed it. This strongly suggests that an NHS ester group was created on the CA molecule (FIG. 16b).

REFERENCES

Bendele, A., Seely, J., Richey, C., Sennello, G., Shopp, G., Renal tubular vacuolation in animals treated with polyethylene-glycol conjugated proteins, Toxicological sciences, 42 (1998) 152-157.

Beranova, M., Wasserbauer, R., Vancurova, D., Stifter, M., Ocenaskova, J., Mora, M., Biomaterials, 11 (2000) 521-524.

Brocchini, S., Polymers in medicine: a game of chess. Drug Discovery Today, 8, (2003) 111-112.

Carlsson, J., Drevin, H. And Axen, R., Biochem Journal, 173, (1978), 723-737.

Cheng T, Wu, M., Wu, P., Chem, J, Roffer, S R., Accelerated clearance of polyethylene glycol modified proteins by anti-polyethylene glycol IgM. Bioconjugate chemistry, 10 (1999) 520-528.

Cho, J. W. and Troy, F. A., PSA engineering: Synthesis of polysialylated neoglycosphingolipid by using the polytransferase from neuroinvasive E. coli K1, Proceedings of National Academic Sciences, USA, 91 (1994) 11427-11431.

Convers, C. D., Lejeune, L., Shum, K., Gilbert, C., Shorr, R. G. L, Physiological effect of polyethylene glycol conjugation on stroma-free bovine hemoglobin in the conscious dog after partial exchange transfusion, Artificial organ, 21 (1997) 369-378.

Dyer, J. R., Use of periodate oxidation in biochemical analysis, Methods of Biochemical Analysis, 3 (1956) 111-152.

Fernandes, A. I., Gregoriadis, G., Polysialylated asparaginase: preparation, activity and pharmacokinetics, Biochimica et Biophysica Acta, 1341 (1997) 26-34.

Fernandes, A. I., Gregoriadis, G., Synthesis, characterization and properties of polysialylated catalase, Biochimica et Biophysica Acta, 1293 (1996) 92-96.

Fernandes, A. I., Gregoriadis, G., The effect of polysialylation on the immunogenicity and antigenicity of asparaginase: implications in its pharmacokinetics, International Journal of Pharmaceutics, 217 (2001) 215-224.

Fleury, P., Lange, J., Sur l'oxydation des acides alcools et des sucres par l'acid periodique, Comptes Rendus Academic Sciences, 195 (1932) 1395-1397.

Furuhata, Trends in Glycosci. Glycotech. 2004, 18(89) 143-169.

Gregoriadis, G., Drug and vaccine delivery systems, in: PharmaTech, World Markets Research Centre Limited, London (2001) 172-176.

Gregoriadis, G., Fernandes, A., McCormack, B., Mital, M., Zhang, X, Polysialic acids: Potential for long circulating drug, protein, liposome and other microparticle constructs, in Gregoriadis, G and McCormack, B (Eds), Targeting of Drugs, Stealth Therapeutic Systems, Plenum Press, New York (1998) 193-205.

Gregoriadis, G., Fernandes, A., Mital, M., McCormack, B., Polysialic acids: potential in improving the stability and pharmacokinetics of proteins and other therapeutics, Cellular and Molecular Life Sciences, 57 (2000) 1964-1969.

Gregoriadis, G., McCormack, B., Wang, Z., Lifely, R., Polysialic acids: potential in drug delivery, FEBS Letters, 315 (1993) 271-276.

Hermanson, G. T., Bioconjugate techniques, Acadamic press, London, 1995.

Hreczuk-Hirst, D., Jain, S., Genkin, D., Laing, P., Gregoriadis, G., Preparation and properties of polysialylated interferon-α-2b, AAPS Annual Meeting, 2002, Toronto, Canada, M1056

Hunter, A. C, Moghimi, S. M., Therapeutic synthetic polymers: a game of Russian Roulette. Drug Discovery Today, 7 (2002) 998-1001.

Jain, S., Hirst, D. H., McCormack, B., Mital, M., Epenetos, A., Laing, P., Gregoriadis, G., Polysialylated insulin: synthesis, characterization and biological activity in vivo, Biochemica et. Biophysica Acta, 1622 (2003) 42-49.

Jain, S., Hirst, D. H., Laing, P., Gregoriadis, G., Polysialylation: The natural way to improve the stability and pharmacokinetics of protein and peptide drugs, Drug Delivery Systems and Sciences, 4(2) (2004) 3-9.

Jennings, H. J., Lugowski, C., Immunogenicity of groups A, B, and C meningococal polysaccharide tetanus toxoid conjugates, Journal of Immunology, 127 (1981) 1011-1018.

Jennings, H. J., et al in J. Immunol. (1986) 137, 1708-1713.

Lifely, R., Gilhert, A. S., Moreno, C. C., Sialic acid polysaccharide antigen of *Neisseria meningitidis* and *Escherichia coli*: esterification between adjacent residues, Carbohydrate Research, 94 (1981) 193-203.

Mital, M., Polysialic acids: a role for optimization of peptide and protein therapeutics, Ph.D. Thesis, University of London, 2004.

Muflenhoff, M., Ectehardt, M., Gerardy-Schohn, R., Polysialic acid: three-dimensional structure, biosynthesis and function, Current opinions in Structural Biology, 8 (1998) 558-564.

Park, J. T., Johnson, M. J., A submicrodetermination of glucose, Journal of Biological Chemistry, 181 (1949) 149-151.

Pawlowski, A. et al. Vaccine 17 (1999) 1474-1483.

Roth, J., Rutishauser, U., Troy, F. A. (Eds.), Polysialic acid: from microbes to man, Birkhäuser Verlag, Basel, Advances in Life Sciences, 1993.

Rutishauser, U., Polysialic acid as regulator of cell interactions in: R. U. Morgoles and R. K. Margalis (eds.), Neurobiology of Glycoconjugates, pp 367-382, Plenum Press, New York, 1989.

Satake, K., et. al., J. Biochem., 47, 654, (1960).

Shriner, R. L., Fuson, R. D. C., Curtin, D. Y., Morill, T. C., The Systematic Identification of Organic Compounds, 6$^{th}$ ed., Wiley, New York, 1980.

Svennerholm, L., Quantitative estimation of sialic acid II: A colorimetric resorcinol-hydrochloric acid method, Biochimca et Biophysica Acta, 24 (1957) 604-611.

Troy, F. A. Polysialylation of neural cell adhesion molecules, Trends in Glycoscience and Glycotechnology, 2 (1990) 430-449.

Troy, F. A., Polysialylation: From bacteria to brain, Glycobiology, 2 (1992) 1-23.

The invention claimed is:

1. A compound which is a polysialic acid (PSA) substrate molecule having at least one of its terminal units derived from a sialic acid unit in which an ester of N-hydroxysuccinimide (NHS) is linked to the unit at either the 2 or 7-carbon of the sialic acid unit, via a linker, said compound having the general formula I, II or III

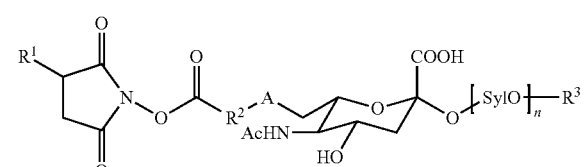

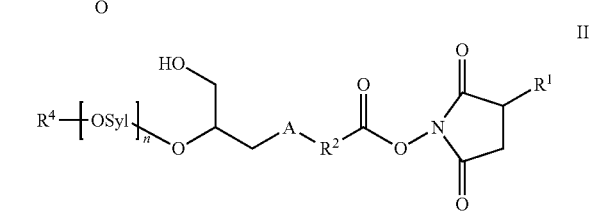

III

[Chemical structure showing compound III with R¹, R², AcHN, HO, COOH groups, and a second structure with HO, SylO, R², R¹ groups]

in which R¹ is H or sulfonyl;
R² is a linking group;
A is NR⁵, NR⁵NR⁶, O or S wherein R⁵ and R⁶ are independently selected from H, $C_{1-4}$ alkyl and aryl;
SylO is a sialyl group;
n is 1-100;
R³ is hydrogen; and
R⁴ is hydrogen.

2. The compound according to claim 1 in which R² is selected from alkanediyl, arylene, alkarylene, heteroarylene, alkyl-heteroarylene any of which may be interrupted by either thioester, ester, amine or amide linkages, and in which A is NR⁵ or a linker group joined to the rest of the molecule through a group NR⁵.

3. A process for forming a compound according to claim 1, which comprises reacting PSA with a bifunctional reagent, said bifunctional reagent comprising a functionality which is an NHS ester and another functionality reactive at the 2 or 7 carbon atom of a terminal sialic acid unit, under conditions such that covalent conjugation between the reagent and the sialic acid unit occurs and the NHS group remains unchanged, said reaction optionally preceded by derivatizing the terminal sialic acid of said PSA.

4. The process according to claim 3 wherein said sialic acid unit in the PSA is derivatized to generate an amine group.

5. The process according to claim 4 wherein terminal sialic acid unit is a reducing terminal unit and where the derivatizing comprises:
   a) reducing the reducing terminal sialic acid unit to form a vicinal diol group;
   b) selectively oxidizing the vicinal diol group formed in step a) to form an aldehyde group;
   c) converting the aldehyde of step b) to an amino group by reductive amination.

6. The process according to claim 4 wherein said PSA having a terminal sialic acid at the non-reducing terminal end is oxidized selectively in the non-reducing terminal sialic acid unit at the C-7, C-8 vicinal diol group to form an aldehyde on carbon atom 7; and converting the aldehyde group to an amino group by reductive amination.

7. The process according to claim 4 in which the NHS reagent is selected from:
   bis[2-succinimidyloxycarbonyl-oxy)ethyl]sulfone (BSOCOES),
   bis(sulfosuccinimidyl)suberate) (BS³),
   disuccinimidyl glutarate (DSG),
   dithiobis (succinimidyl propionate) (DSP),
   disuccinimidyl suberate (DSS),
   disuccinimidyl tartrate (DST) or its sulfo analog,
   3,3'-dithiobis (sulfosuccinimidyl propionate) (DTSSP), and
   ethylene glycol bis(succinimidyl succinate) (EGS) or its sulfo analog.

8. The process according to claim 7 in which the reaction with the NHS reagent is carried out in aprotic solvent.

9. The process according to claim 3 in which the sialic acid unit is subjected to a preliminary step in which a thiol group is generated.

10. The process according to claim 9 in which the NHS reagent is selected from:
    N-(α-maleimidoacetoxy)succinimide ester(AMAS),
    N-(β-maleimidopropyloxy)succinimide ester (BMPS),
    N-(ξ-maleimidocapryloxy)succinimide ester (EMCS) or its sulfo analog,
    N-(γ-maleimidobutyryloxy)succinimide ester (GMBS) or its sulfo analog,
    succinimidyl-4-(N-maleimidomethyl)-cyclohexane-1-carboxy-(6-amidocaproate) (LC-SMCC),
    m-maleimido benzoyl-N-hydroxysuccinimide ester (MBS) or its sulfo analog,
    succinimidyl-4-(N-maleimidomethyl)-cyclohexane-1-carboxyate) or its sulfo analog,
    succinimidyl-4-(p-maleimido phenyl)butyrate (SMBP) or its sulfo analog,
    succinimidyl-6-(β-maleimido-propionamido) hexanoate (SMPH),
    N-(k-maleimidoundecanoyloxy) sulfosuccinimide-ester (sulfo-KMUS),
    succinimidyl 6-[3-2(2-pyridyldithio)-propionamido]hexanoate (LC-SPDP) or its sulfo analog,
    4-succinimidyloxycarbonyl-methyl-α-(2-pyridyldithio) toluene (SMPT),
    N-succinimidyl-3-(2-pyridyldithio)propionate (SPDP),
    N-succinimidyl [4-vinylsulfonyl)benzoate (SVSB),
    succinimidyl 3-(bromoacetamido)propionate (SBAP),
    N-succinimidyliodoacetate (SIA), and
    N-succinimidyl(4-iodoacetyl)aminobenzoate (SIAB) or its sulfo analog.

11. A method comprising reacting a biologically useful compound having a primary amine group with the compound of claim 1 under conditions in which the active hydrogen of the amine is replaced by the acyl group remaining after the N-succinimidyloxy group is replaced.

12. The method according to claim 11 in which the biologically useful molecule is a protein or peptide of which the primary amine group is the N-terminus or is the γ-amino group of a lysine unit.

13. A method which comprising reacting a biologically useful compound having a primary amine group with the product of a process of claim 3 under conditions in which the active hydrogen of the amine is replaced by the acyl group remaining after the N-succinimidyloxy group is replaced.

14. The method according to claim 13 in which the biologically useful molecule is a protein or peptide of which the primary amine group is the N-terminus or is the γ-amino group of a lysine unit.

* * * * *